United States Patent [19]

Freyne et al.

[11] Patent Number: 5,541,325
[45] Date of Patent: Jul. 30, 1996

[54] INTERMEDIATES FOR THE PREPARATION OF 1,3,DIHYDRO-2H-IMIDAZO[4,5-B] QUINOLIN-2-ONE DERIVATIVES

[75] Inventors: Eddy J. E. Freyne, Rumst; Alfons H. M. Raeymaekers; Didier R. G. G. de Chaffoy de Courcelles, both of Beerse, all of Belgium

[73] Assignee: Janssen Pharmaceutica N.V., Beerse, Belgium

[21] Appl. No.: 423,920

[22] Filed: Apr. 18, 1995

Related U.S. Application Data

[60] Division of Ser. No. 204,412, Mar. 15, 1994, and a continuation-in-part of Ser. No. 784,955, filed as PCT/EP92/02496, Oct. 27, 1992, abandoned.

[51] Int. Cl.$^6$ .................... C07D 401/10; C07D 413/10; C07D 215/38; C07F 7/10
[52] U.S. Cl. .................... 544/363; 544/128; 546/14; 546/159; 546/82
[58] Field of Search .................... 546/159, 14; 544/128, 544/363

[56] References Cited

U.S. PATENT DOCUMENTS

| | | | |
|---|---|---|---|
| 4,701,459 | 10/1987 | Meanwell et al. | 514/293 |
| 4,943,573 | 7/1990 | Meanwell | 514/253 |
| 5,043,327 | 8/1991 | Freyne et al. | 514/63 |
| 5,342,842 | 8/1994 | Cheng | 514/274 |

FOREIGN PATENT DOCUMENTS

| | | |
|---|---|---|
| 426180 | 5/1991 | European Pat. Off. |
| 541153 | 5/1993 | European Pat. Off. |
| 2174987 | 11/1986 | United Kingdom . |
| 2190676 | 11/1987 | United Kingdom . |

OTHER PUBLICATIONS

Meanwell et al, *J. Med. Chem.* 35, pp. 2672–2687 (Jul. 10, 1992).
Beavo et al, *TIPS* 11 pp. 150–155 (1990).
Nicholson et al, *TIPS* 121 pp. 19–27 (1991).

*Primary Examiner*—Emily Bernhardt
*Attorney, Agent, or Firm*—Charles J. Metz

[57] ABSTRACT

The present invention relates to compounds of the formula

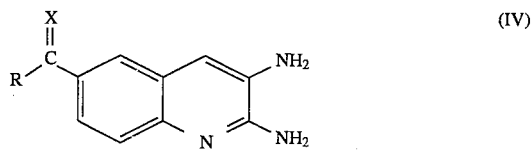

(IV)

wherein R represents hydrogen; $C_{1-6}$alkyl; $C_{3-6}$cycloalkyl; phenyl optionally substituted with from 1 to 3 substituents each independently selected from halo, hydroxy, $C_{1-6}$alkyloxy, $C_{5-6}$cycloalkyloxy, $C_{1-6}$alkyl or trifluoromethyl; pyridinyl; or thienyl optionally substituted with halo or $C_{1-6}$alkyl; and =C=X is a radical of the formula:

=C=O            (a),

=C=N—O—R$^1$     (b), or

=C=CH—R$^2$      (c);

the addition salts thereof and stereochemically isomeric forms thereof, said compounds being useful as intermediate to potent inhibitors of both phosphodiesterase III and IV, which are useful in the treatment of warm-blooded animals suffering from allergic disorders, atopic diseases and related afflications.

4 Claims, No Drawings

INTERMEDIATES FOR THE PREPARATION OF 1,3-DIHYDRO-2H-IMIDAZO[4,5-B]QUINOLIN-2-ONE DERIVATIVES

CROSS-REFERENCE TO RELATED APPLICATIONS

This application is a divisional of application Ser. No. 08/204,412, filed Mar. 15, 1994, now U.S. Pat. No. 5,521,187, which was based upon PCT application No. PCT/EP 92/02496, filed Oct. 27, 1992, which claims priority as a continuation-in-part from U.S. application Ser. No. 07/784,955, filed Oct. 30, 1991, now abandoned.

BACKGROUND OF THE INVENTION

A number of substituted imidazo[4,5-b]quinolin-2-ones are known from BE-904,671; DE-A-3,717,291; U.S. Pat. Nos. 4,710,459 and 4,943,573 as phosphodiesterase and blood platelet aggregation inhibitors which are useful as isotropic cardiotonics and antithrombotics.

In U.S. Pat. No. 5,043,327 which corresponds to EP-A-0,406,958, published Jan. 9, 1991, there are described positive isotropic and lusitropic 3,5-dihydro-imidazo[2,1-b]quinazolin-2(1H)-one derivatives.

DESCRIPTION OF THE INVENTION

The present invention is concerned with novel 1,3-dihydro-2H-imidazo[4,5-b]quinolin-2-one derivatives having the formula

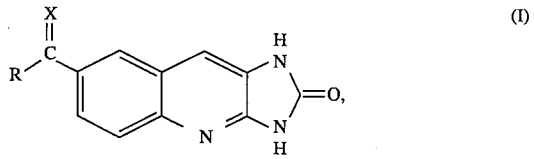

the pharmaceutically acceptable addition salts thereof and the stereochemically isomeric forms thereof, wherein R is hydrogen, $C_{1-6}$alkyl, $C_{3-6}$cycloalkyl, phenyl optionally substituted with from 1 to 3 substituents each independently selected from halo, hydroxy, $C_{1-6}$alkyloxy, $C_{5-6}$cycloalkyloxy, $C_{1-6}$alkyl or trifluoromethyl; pyridinyl; thienyl optionally substituted with halo or $C_{1-6}$alkyl;

>C=X is a radical of formula

$R^1$ is hydrogen, tri($C_{1-6}$alkyl)silyl or $C_{1-6}$alkyl optionally substituted with COOH, COO$C_{1-4}$alkyl, CONR$^3$R$^4$ or COOCH$_2$CONR$^5$R$^6$;

$R^2$ is COOH, COO$C_{1-4}$alkyl, CONR$^3$R$^4$, COOCH$_2$CONR$^5$R$^6$ or $C_{1-6}$alkyl optionally substituted with COOH, COO$C_{1-4}$alkyl, CONR$^3$R$^4$ or COOCH$_2$CONR$^5$R$^6$;

$R^3$ is hydrogen, $C_{1-4}$alkyl, hydroxy$C_{1-4}$alkyl, $C_{1-4}$alkyloxy$C_{1-4}$alkyl, hydroxy-carbonyl$C_{1-4}$alkyl, $C_{1-4}$alkyloxycarbonyl$C_{1-4}$alkyl;

$R^4$ is hydrogen, $C_{1-4}$alkyl, hydroxy$C_{1-4}C_{1-4}$alkyl, $C_{3-7}$cycloalkyl, phenyl, thienyl or pyridinyl; or $R^3$ or $R^4$ taken together with the nitrogen atom to which they are attached may form a pyrrolidinyl, morpholinyl or piperazinyl ring, said piperazinyl ring being optionally substituted on the nitrogen atom with $C_{1-4}$alkyl, ($C_{3-7}$cycloalkyl)$C_{1-4}$alkyl, phenyl$C_{1-4}$alkyl or $C_{1-6}$alkyl substituted with one, two, three, four or five hydroxy groups; and $R^5$ is hydrogen, $C_{1-4}$alkyl, hydroxy$C_{1-4}$alkyl, $C_{1-4}$alkyloxy$C_{1-4}$alkyl, hydroxycarbonyl$C_{1-4}$alkyl, $C_{1-4}$alkyloxycarbonyl$C_{1-4}$alkyl;

$R^6$ is hydrogen, $C_{1-4}$alkyl, hydroxy$C_{1-4}$alkyl, $C_{3-7}$cycloalkyl, phenyl, thienyl or pyridinyl; or $R^5$ and $R^6$ taken together with the nitrogen atom to which they are attached may form a pyrrolidinyl, morpholinyl or piperazinyl ring, said piperazinyl ring being optionally substituted on the nitrogen atom with $C_{1-4}$alkyl, ($C_{3-7}$cycloalkyl)$C_{1-4}$alkyl, phenyl$C_{1-4}$alkyl or $C_{1-6}$alkyl substituted with one, two, three, four or five hydroxy groups.

In the foregoing definitions the term halo defines fluoro, chloro, bromo and iodo; $C_{1-4}$alkyl defines straight and branched saturated hydrocarbon radicals having from 1 to 4 carbon atoms, such as, for example, methyl, ethyl, propyl, 1-methylethyl, butyl, 1-methylpropyl, 2-methylpropyl and 1,1-dimethylethyl; $C_{1-6}$alkyl defines $C_{1-4}$alkyl and the higher homologs thereof such as, for example, pentyl, hexyl and the like; $C_{3-7}$cycloalkyl defines cyclopropyl, cyclobutyl, cyclopentyl, cyclohexyl and cycloheptyl. Tri($C_{1-6}$alkyl)silyl in particular may be trimethylsily, triethylsily, tert.

Pharmaceutically acceptable addition salts as mentioned hereinabove comprise the therapeutically active non-toxic addition salt forms which the compounds of formula (I) are able to form. Said salt forms can conveniently be obtained by treating the base form of the compounds of formula (I) with appropriate acids such as inorganic acids, for example, hydrohalic acid, e.g., hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may also be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt also comprises the hydrates and solvent addition forms which the compounds of formula (I) are able to form. Examples of such forms are e.g. hydrates, alcoholates and the like.

The compounds of this invention may be asymmetric carbon atoms in their structure. Each of these chiral centers may be indicated by the stereochemical descriptors R and S. The compounds of formula (I) wherein >C=X is a radical of formula (b) or (c) may occur as mixtures of E- and Z-forms or as pure E-forms or pure Z-forms.

Pure stereochemically isomeric forms of the compounds of formula (I) may be obtained by the application of art-known procedures. Diastereoisomers may be separated by physical methods such as selective crystallization and chromatographic techniques, e.g. counter current distribution, liquid chromatography and the like; and enantiomers by the selective crystallization of their diastereomeric salts with chiral acids. Alternatively, the enantiomers may be separated by liquid chromatography using a chiral stationary phase. Pure stereochemically isomeric forms may also be derived from the corresponding pure stereochemically isomeric forms of the appropriate starting materials, provided that the reactions occur stereospecifically. Preferably, if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

Interesting compounds are those compounds of formula (I) wherein R is hydrogen; phenyl optionally substituted with 1 or 2 substituents each independently selected from halo, $C_{1-6}$alkyloxy, $C_{5-6}$cycloalkyloxy or $C_{1-6}$alkyl; pyridinyl; and >C=X is a radical of formula (a) or (b).

More interesting compounds are those interesting compounds where R is hydrogen phenyl, optionally substituted with 1 or 2 substituents each independently selected from fluoro, chloro, bromo, methoxy, cyclopentyloxy or methyl; pyridinyl; and >C=X is a radical formula (a) or (b), wherein $R^1$ is $C_{1-4}$alkyl optionally substituted with COOH, $COOC_{1-4}$alkyl or $CONR^3R^4$.

Particularly interesting compounds are those more interesting compounds wherein R is hydrogen or pheyl optionally substituted with 1 or 2 substituents each independently selected from fluoro, methoxy or methyl; and >C=X is a radical of formula (a) or (b) wherein $R^1$ is $C_{1-4}$alkyl optionally substituted with COOH, $COOC_2H_5$.

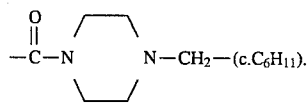

The most interesting compounds within the present invention are:

(E)-N-cyclohexyl-2-[[[(2,3-dihydro-2-oxo-1H-imidazo[4,5-b]quinolin-7-yl)phenylmethylene]amino]oxy]-N-methyacetamide;

7-benzoyl-1,3-dihydro-2H-imidazo[4,5-b]quinolin-2-one;

(E)-1-(cyclohexylmethyl)-4-[[[[(2,3-dihydro-2-oxo-1H-imidazo[4,5-b]quinolin-7-yl) methylene]amino]oxy]acetyl] piperazine; or (E)-N-cyclohexyl-2-[[[(2,3-dihydro-2-oxo-1H-imidazo[4,5-b]quinolin-7-yl)methylene]amino]oxy]-N-methylacetamide; the pharmaceutically acceptable addition salts thereof and the stereochemically isomeric forms thereof.

In order to simplify the structural representation of the compounds and of some of the intermediates in the following preparations, the 1,3-dihydro-2H-imidazo[4,5-b]quinolin-2-one moiety will hereinafter be represented by the symbol D.

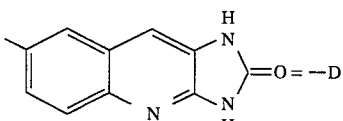

The compounds of formula (I) can generally be prepared by cyclizing an intermediate of formula (II)

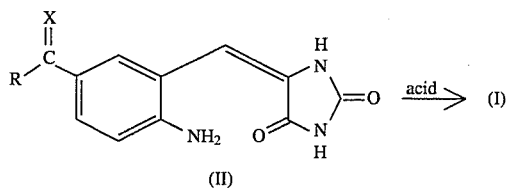

in a suitable solvent such as e.g. dimethylsulfoxide, N,N-dimethylacetamide, tetrahydrothiophene, 1,1-dioxide, diphenylether and the like, in the presence of an acid such as, for example, acetic acid, trifluoroacetic acid or a sulfonic acid, e.g. methanesulfonic acid, trifluoromethanesulfonic acid, 4-methylbenzenesulfonic acid or pyridinium 4-methylbenezesulfonate and the like. In some instances it may be appropriate to employ an excess of acid as solvent. Further, in order to enhance the rate of the reaction, said cyclization reaction may advantageously be conducted at a temperature between 130° C. and 160° C., preferably between 140° C. and 150° C.

The compounds of formula (I) can also be prepared by cyclizing an intermediate of formula (III)

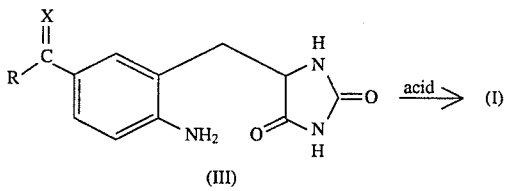

according to the procedures described above for cyclizing an intermediate of formula (II).

Converting an intermediate of formula (III) into a compound of formula (I), however, involves an aromatization process, wherein the solvent may act as an oxidant. In order to effect full aromatization, iodine may be added to the reaction mixture as an oxidant, either during or preferably upon completion of the cyclization reaction. In some instances, the saturated intermediate having the following chemical structure

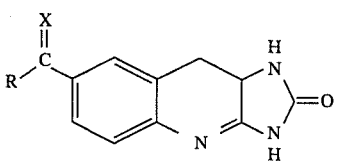

can be formed upon reacting the intermediates of formula (III) in the presence of an acid. Said saturated intermediate may then be oxidized into a compound of formula (I) following art-known procedures.

Cyclizing an intermediate of formula (III) into a compound of formula (I) offers an important advantage over the previous cyclization procedure: whereas only the E-isomers of (II) will give cyclization, no such isomers of (III) are involved and a much higher yield of (I) can be obtained.

Further, the compounds of formula (I) may be prepared by reacting an intermediate of formula (IV) with a reagent of formula (V) wherein W is a reactive leaving group, such as, for example, halo, amino, $C_{1-4}$alkyloxy, imidazolyl, triazolyl, and the like, in a reaction-inert solvent.

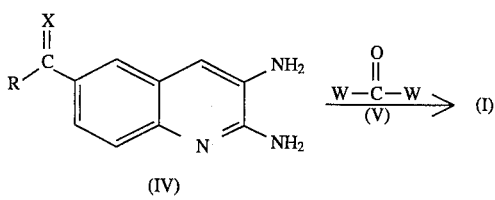

An appropriate solvent for the above reaction is, for example, a halogenated hydrocarbon, e.g. dichloromethane, trichloromethane and the like; an aromatic hydrocarbon, e.g. benzene, methylbenzene and the like; an ether, e.g. 1,1'-oxybisethane, tetrahydrofuran and the like; a dipolar aprotic solvent e.g. N,N-dimethylformamide, N,N-dimethylacetamide, acetonitrile and the like.

The compounds of formula (I-b) and (I-c)

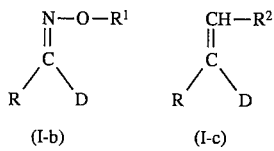

wherein $R^1$ is $C_{1-6}$alkyl substituted with COOH, $COOC_{1-4}$alkyl, $CONR^3R^4$ or $COOCH_2CONR^5R^6$, and $R^2$ is COOH, $COOC_{1-4}$alkyl, $CONR^3R^4$ or $COOCH_2CONR^5R^6$, each may be converted among themselves following art-known procedures such as, for example, esterification, amidation, transesterification, transamidation, ester hydrolysis and the like methods.

For example, the compounds where $R^1$ or $R^2$ is $C_{1-6}$alkyl substituted with COOH or $R^2$ is COOH may be converted into an ester wherein $R^1$ or $R^2$ is $C_{1-6}$alkyl substituted with $COOC_{1-4}$alkyl or $COOCH_2CONR^5R^6$, or $R^2$ is $COOC_{1-4}$alkyl or $COOCH_2CONR^5R^6$, or into an amide wherein $R^1$ or $R^2$ is $COOC_{1-4}$alkyl or $CONR^3R^4$ or $R^2$ is $CONR^3R^4$ by treating the carboxylic acid with an alkanol of formula $C_{1-4}$alkyl—OH or an alcohol of formula $HOCH_2CONR^5R^6$ or an amine of formula $HNR^3R^4$ in the presence of a suitable reagent capable of forming esters and/or amides. Typical examples of such reagents are for example, dicyclohexylcarbodiimide, 2-chloro-1-methylpyridinium iodide, phosphorus pentoxide, 1,1'-carbonylbis[1H-imidazole], 1,1'-sulfonylbis[1H-imidazole] and the like reagents. Alternatively, said carboxylic acids may be converted into suitable reactive functional derivatives thereof such as, for example, an acyl halide, symmetric or mixed anhydride, ester, amide, acyl azide, cyclic anhydride, lactone, lactam and the like derivatives before reaction with the alkanol $C_{1-4}$alkyl—OH, the alcohol of formula $HOCH_2CONR^5R^6$ or the amine $HNR^3R^4$. Said reactive functional derivatives may be prepared following art known methods, for example, by reacting the carboxylic acid with a halogenating reagent such as, for example, thionyl chloride, phosphorous trichloride, polyphosphorous acid, phosphoryl chloride, oxalyl chloride and the like, or be reacting said carboxylic acid with an acyl halide such as acetyl chloride and the like. Said reactive functional derivatives of the carboxylic acids may be generated in situ, or if desired, be isolated and further purified before reacting them with the alkanol $C_{1-4}$alkyl—OH, the alcohol of formula $HOCH_2CONR^5R^6$ or the amine $HNR^3R^4$.

Said esterification and amidation reactions can conveniently be carried out by stirring the reactants, optionally in a suitable reaction-inert solvent such as, for example, a halogenated hydrocarbon, e.g. dichloromethane, trichloromethane and the like; an aromatic hydrocarbon, e.g. benzene methylbenzene and the like; an ether, e.g. 1,1'-oxybisethane, tetrahydrofuran and the like; or a dipolar aprotic solvent, e.g. N,N-dimethylformamide, N,N-dimethylacetamide, pyridine and the like. In some instances it may be appropriate to employ an excess of one of the reagents as solvent the water, acid, alcohol or amine which is liberated during the course of the reaction may be removed from the reaction mixture by art-known procedures such as, for example, azeotropical distillation, complexation, salt formation and the like methods. In some instances particularly the addition of a suitable base such as, for example, an amine, e.g. N,N-diethylethanamine, 4-ethylmorpholine, pyridine or N,N-dimethyl-4-pyridinamine, may be appropriate. Further, in order to enhance the rate of the reaction, said acylation reaction may advantageously be conducted at a somewhat elevated temperature, in particular the reflux temperature of the reaction mixture.

Transesterification may be accomplished by reacting a compound wherein $R^1$ and $R^2$ is $C_{1-6}$alkyl substituted with $COOC_{1-4}$alkyl or $COOCH_2CONR^5R^6$ or $R^2$ is $COOC_{1-4}$alkyl or $COOCH_2CONR^5R^6$, with a different alkanol of formula $C_{1-4}$alkylOH or a different alcohol of formula $HOCH_2CONR^5R^6$. The equilibrium of the transesterification reaction may be shifted following art-known methods, e.g. by using an excess of said alcohol, or by distilling off the liberated alcohol. Transamination can be accomplished in a similar manner by reaction with an amine $HNR^3R^4$.

The compounds wherein $R^1$ and $R^2$ is $C_{1-6}$alkyl substituted with $COOC_{1-4}$alkyl or $COOCH_2CONR^5R^6$ or $R^2$ is $COOC_{1-4}$alkyl or $COOCH_2CONR^5R^6$ can be hydrolysed to the corresponding compounds wherein $R^1$ or $R^2$ is $C_{1-6}$alkyl substituted with COOH or $R^2$ is COOH Said hydrolysis can conveniently be conducted by stirring and heating the ester in an aqueous and/or alcoholic medium, e.g., water, methanol, ethanol and the like, or mixtures thereof, in the presence of a base such as, for example, sodium hydroxide, potassium hydroxide, potassium carbonate and the like. In some instances, for example, the 1,1-dimethylethyl ester, said hydrolysis may also be effected by stirring and optionally heating in an acidic aqueous and/or alcoholic medium as defined hereinabove.

The compounds of formula (I) wherein >C=X is a radical of formula (b), said compounds being represented by formula (I-b), may be obtained by reacting a compound of formula (I) wherein >C=X is a radical of formula (a), said compound being represented by formula (I-a), with an appropriate hydroxylamine derivative of formula (VI) or an acid addition salt thereof.

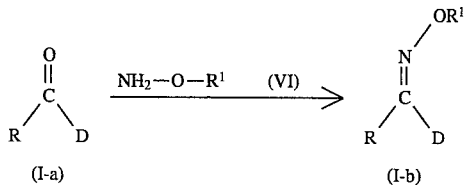

Said reaction can be carried out by stirring and heating the reagents in an appropriate solvent an an elevated temperature, in particular the reflux temperature of the reaction mixture. Appropriate solvents are for example, aromatic hydrocarbons, e.g. benzene, methylbenzene, dimethylbenzene and the like; halogenated hydrocarbons, e.g. trichloromethane, tetrachloromethane and the like; ethers e.g. 1,1'-oxybisethane, tetrahydrofuran, 1,4-dioxane and the like; alcohols, e.g. methanol, ethanol, 2-propanol saturated with hydrochloric acid; esters, e.g. ethyl acetate, butyl acetate and the like; dipolar aprotic solvents, e.g. N,N-dimethylformamide, N,N-dimethylacetamide, acetonitrile, pyridine and the like, or mixtures thereof.

The compounds of formula (I) wherein =C=X is a radical of formula (c), said compounds being represented by formula (I-c), may be prepared by reacting the compounds of formula (I-a) with a phosphorus ylide of formula (VII) (Wittig reaction) or with an ylide of formula (VIII) prepared from a phosphonate (Horner-Emmons reaction).

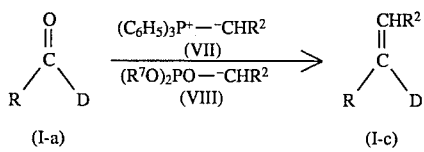

In formula (VIII) $R^7$ represents $C_{1-6}$alkyl. The reaction can conveniently be conducted by treating a phosphonium salt or a phosphonate with an appropriate base such as, for example, sodium, butyllithium, methyllithium, N,N-diethylethanamine, acetonitrile, sodium amide, sodium hydride, a sodium or potassium alkoxide, sulfinylbis(methane) sodium salt and the like bases, under an inert atmosphere and in a reaction-inert solvent such as for example, a hydrocarbon, e.g. hexane, heptane, cyclohexane and the like; an ether, e.g. 1,1'oxybisethane, tetrahydrofuran, 1,2-dimethoxyethane and the like; an alcohol, e.g. ethanol and the like; a dipolar aprotic solvent, e.g. dimethylsulfoxide, hexamethylphosphor triamide, and the like solvents; and subsequently treating the thus obtained ylides (VII) or (VIII) with the compound of formula (I-a), optionally at a slightly elevated temperature.

Alternatively the compounds of formula (I-c) may be prepared by reacting a compound of formula (I-a) with an organometallic reagent of formula (IX) wherein M represents a metal group such as, for example, halomagnesium, copper lithium and the like; and subsequently dehydrating the alcohol of formula (X), for example by treatment with an appropriate acid, e.g. hydrochloric or sulfuric acid in a solvent.

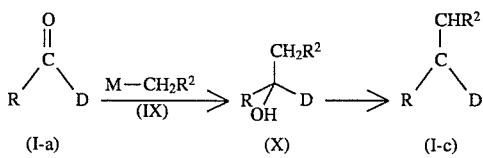

The organometallic reagent may conveniently be prepared following art-known methods by reacting an appropriate halide with a metal such as lithium or magnesium in a reaction-inert solvent such as, for example, an ether, e.g. 1,1'-oxybisethane, tetrahydrofuran, 1,2-dimethoxyethane and the like; an aromatic hydrocarbon, e.g. benzene, methylbenzene and the like.

The compound of formula (I-b) wherein $R^1$ is other than hydrogen, said radical being represented by formula $R^{1-a}$ and said compounds by formula (I-b-1) may also be obtained from compounds of formula (I-b) wherein $R^1$ is hydrogen, said compounds being represented by formula (I-b-2), by O-alkylation or O-silylation with an appropriate alkylating or silylating reagent of formula $R^{1-a}$-$W^1$.

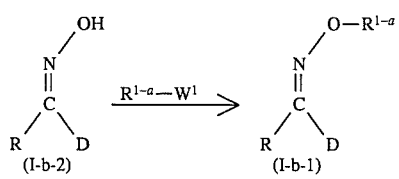

In said alkylating or silylating reagent, $W^1$ represents a leaving group such as, for example, halo, e.g. chloro, bromo, iodo or sulfonyloxy, e.g. 4-methylbenzenesulfonyloxy, benzenesulfonyloxy, 2-naphthalenesulfonyloxy, methanesulfonyloxy, trifluoromethanesulfonyloxy and the like leaving groups. Said O-alkylation and O-silylation reaction can conveniently be conducted by stirring the reactants in a reaction-inert solvent in the presence of a base. Appropriate solvents are halogenated hydrocarbons such as, for example, dichloromethane, trichloromethane and the like; ethers, e.g. 1,1'-oxybisethane, tetrahydrofuran and the like; dipolar aprotic solvents, e.g. N,N-dimethylformamide, N,N-dimethylacetamide, pyridine, acetonitrile; and the like solvents. Suitable bases are amines such as, for example, N,N-diethylethanamine, 4-methylmorpholine, imidazole, pyridine, tetramethylguanidine and the like, or sodium hydride and the like.

Furthermore, the compounds of formula (I-b-2) which may occur as E- or Z-forms or mixtures thereof, may be isomerized by equilibration in an acidic medium.

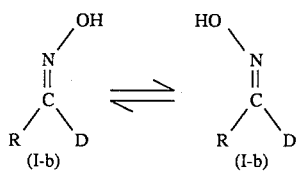

The compounds of formula (I-b-1) wherein $R^{1-a}$ is tri($C_{1-6}$alkyl)silyl may be desilylated to the oximes of formula (I-b-2) by treatment with a fluoride salt such as, for example, potassium fluoride, tetrabutyl ammonium fluoride, or by reaction with hydrofluoric acid, in a solvent such as an ether, e.g. 1,1'-oxybisethane, tetrahydrofuran; or in an aqueous mixture thereof. As the compounds of formula (I-b-1) wherein $R^{1-a}$ is tri($C_{1-6}$alkyl)silyl can easily be separated in the E- and Z-stereoisomers following art-known procedures such as selective crystallization and chromatography, and desilylated as described hereinabove, this sequence provides an efficient procedure for preparing those stereomers of (I-b) which can not be prepared by the isomerization procedure mentioned hereinabove.

Alternatively the compounds of formula (I-b-1) may be prepared from an intermediate of formula (XI) wherein $W^2$ represents a suitable reactive leaving a group such as, for example, halo, e.g. chloro, or acetate, by reaction with a reagent of formula (XII).

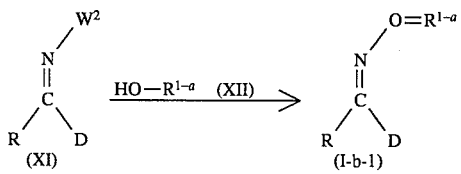

Most key-intermediates of the previous reaction schemes as well as many of their precursors are novel and have especially been developed for conversion into the compounds of the present invention.

The intermediates of formula (II) can be obtained from the corresponding nitro derivatives of formula (XIII) following art-known reduction procedures.

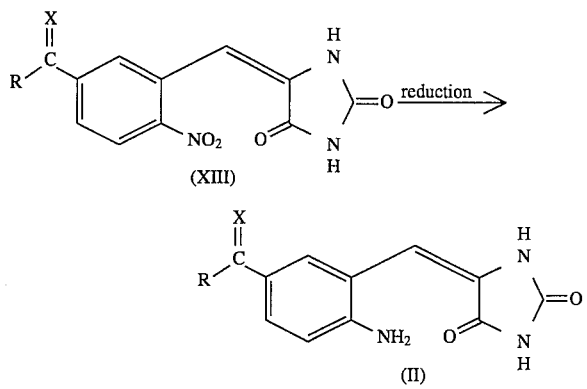

For example, the nitro derivative of formula (XIII) can be reduced by catalytic hydrogenation in a suitable solvent, such as, for example, an alcohol, e.g. methanol, ethanol, an ether, e.g. tetrahydrofuran or 2-methoxyethanol, an ester, e.g. ethyl acetate, a carboxylic acid, e.g. acetic acid, and the like solvents, in the presence of hydrogen, an appropriate catalyst, e.g. platinum-on charcoal, palladium-on-charcoal, Raney nickel and the like, and an appropriate catalyst poison such as thiophene, optionally at an increased temperature and/or pressure. Alternatively, said nitro derivative (XIII) may also be reduced by a reducing agent such as, for example, sodium sulfide, sodium hydrogen sulfide, sodium hydrosulfite, titanium trichloride, trialkylammonium formate-palladium-on-charcoal; iron-ammonium chloride and the like.

The intermediates of formula (III) can be obtained from the intermediate of formula (XIII) by catalystic hydrogenation as described hereinabove, however, without the use of a catalyst poison. Obviously, the intermediates of formula (III) can also be obtained by further reduction of an intermediate of formula (II) e.g catalytic hydrogenation as described hereinabove.

The intermediate nitro derivative of formula (XIII) can be prepared by reacting an intermediate of formula (XIV) with a phosphorus ylide of formula (XV) (Wittig reaction) or with an ylide of formula (XVI) prepared from a phosphonate (Horner-Emmons reaction), wherein $R^7$ represents $C_{1-6}$alkyl,

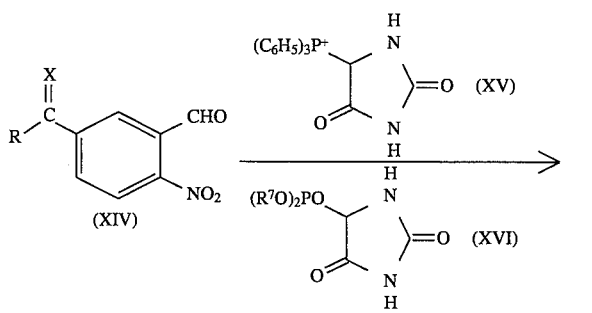

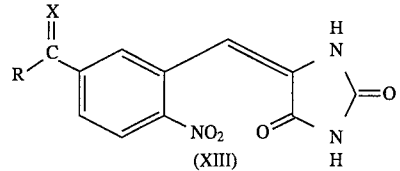

according to the procedure described hereinabove for the preparation of the compounds of formula (I-c).

The intermediates of formula (XIII) may also be prepared by condensing (XIV) with hydantoin (XVII) following art-known procedures, e.g. by treating the reactants with sodium acetate in acetic anhydride or with a base such as, for example, an alkali metal alkoxide, e.g. sodium methoxide, sodium ethoxide, potassium tert. butoxide and the like in an appropriate solvent such as an alcohol, e.g. methanol, ethanol, tert. butanol and the like.

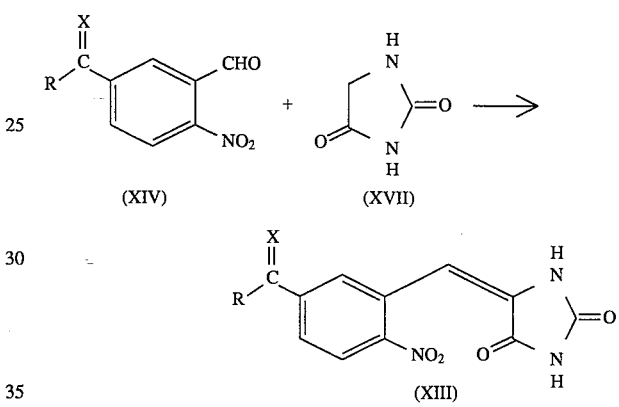

Said condensation reaction may conveniently be conducted by stirring and gently heating the reaction mixture.

The intermediates of formula (XIV) wherein >C=X is a radical of formula (a), said intermediates being represented by formula (XIV-a), can be obtained from an intermediate of formula (XVIII), wherein both $R^8$ radicals represent an alkyl group, such as methyl, ethyl and the like, or both $R^8$ taken together from an alkanediyl radical such as, 1,2-ethanediyl, 1,3-propanediyl, 2,2-dimethyl-1,3-propanediyl and the like, by hydrolysis in an acidic aqueous medium.

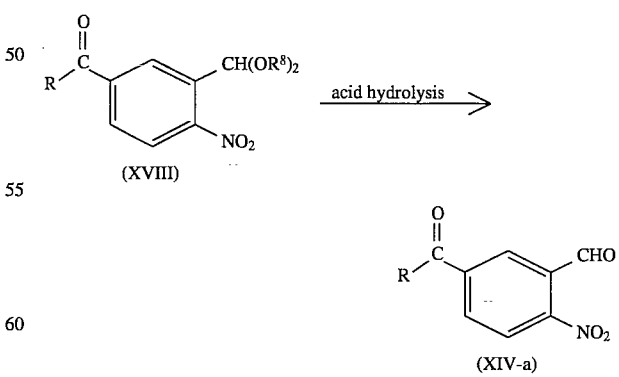

The intermediates of formula (XVIII) can be prepared from a cyanide of formula (XIX) following art-known oxidation procedures such as aerating (XIX) in a basic medium.

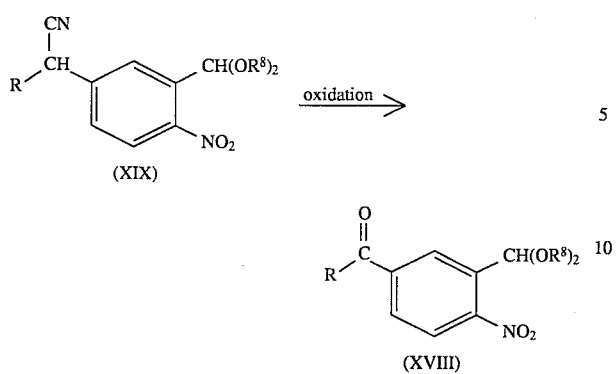

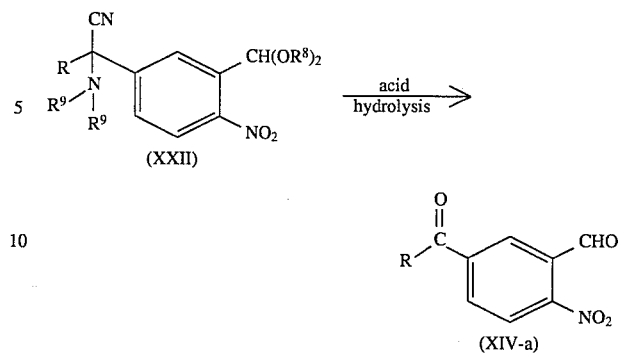

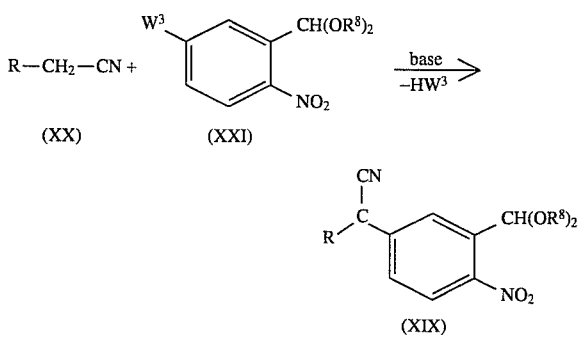

The cyanides of formula (XIX) can easily be obtained by an aromatic nucleophilic substitution reaction of a cyanide of formula (XX) on a nitrobenzene of formula (XXXI).

In formula (XXII) and hereinafter the group —NR$^9$R$^9$ represents a dialkylamino group or a heterocyclic radical such as, for example, morpholino, piperidino, pyrrolidino and the like groups.

The intermediate of formula (XXII) in turn can be prepared by an aromatic nucleophilic substitution reaction on a nitrobenzene of formula (XXI) as described hereinabove for the preparation of the intermediates of formula (XIX).

In formula (XXI) W$^3$ represents a reactive leaving group such as, for example, halo, e.g. chloro or fluoro, nitro, 4-methylbenzenesulfonyloxy, phenyloxy, alkyloxy and the like groups known in the art to be good leaving groups in aromatic nucleophilic substitution reactions. Said aromatic nucleophilic substitution reaction can conveniently be conducted by stirring the reactants in the presence of a base in a reaction-inert solvent such as, for example, a dipolar aprotic solvent, e.g. N,N-dimethylformamide, N,N-dimethylacetamide, hexamethylphosphoric triamide, pyridine, 1,3-dimethyl-3,4,5,6-tetrahydro-2-(1H)-pyrrolidinone, 1,3-dimethylimidazolidinone, 1,1,3,3-tetramethylurea, 1-methyl-2-pyrrolidinone, nitrobenzene and the like solvents; or mixtures thereof. Appropriate base are sodium hydride, sodium amide, sulfinylbis(methane) sodium salt, lithium diisopropylamide and the like bases. It may be advantageous to add to the reaction mixture a crown ether, e.g. 1,4,7,10,13,16-hexaoxacyclooctadecane and the like or a complexing agent such as for example, tris[2-(2-methoxyethoxy)]ethanamine and the like. Somewhat elevated temperatures may enhance the rate of the reaction. Alternatively, said aromatic nucleophilic substitution reaction may be carried out by applying art-known conditions of phase transfer catalysis reactions. Said conditions comprise stirring the reactants, with an appropriate base, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts.

The aldehydes of formula (XIV-a) can also be obtained by hydrolyzing in an aqueous medium an α-aminocyanide of formula (XXII).

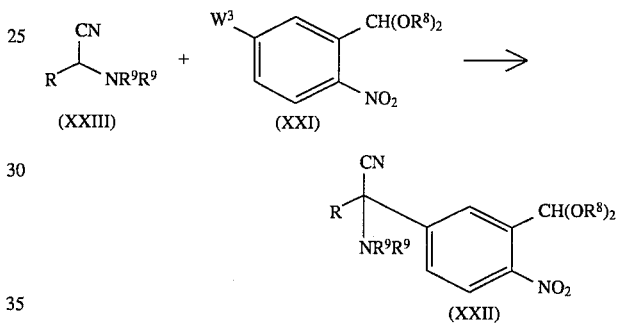

The reagent of formula (XXIII) can easily be prepared from an appropriate aldehyde by reaction with sodium cyanide, potassium cyanide and the like cyanides, in the presence of an amine HNR$^9$R$^9$ and sodium hydrogen sulfite. Suitable solvents are for example, eater, alkanols, e.g. methanol, ethanol and the like, and mixtures thereof.

Alternatively, the intermediates of formula (XIV-a) can also be prepared by oxidation of the corresponding alcohol of formula (XXIV) following art-known oxidation procedures.

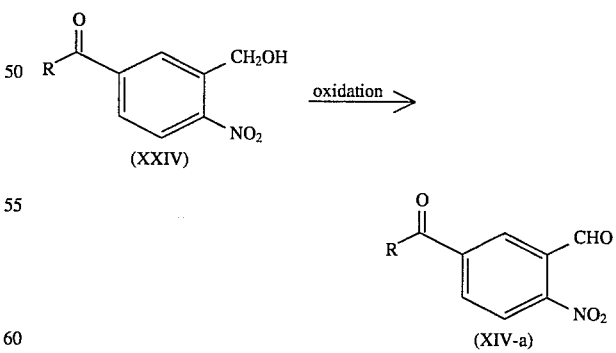

Said oxidation reaction can conveniently be conducted by stirring the reactant in a reaction-inert solvent, e.g. dimethylsulfoxide, dichloromethane and the like or a mixture thereof, in the presence of an oxidizing agent such as, for example, manganese(IV)-oxide, pyridinium dichromate and the like. Said oxidation may also be conducted by treating the alcohol at a low temperature, preferably at −60° C. with a reactive complex prepared from dimethylsulfoxide and a reagent such as, for example, dicyclohexylcarbodiimide, chlorosulfonyl isocyanate, oxalyl chloride, molybdenum peroxide 4-methylbenzenesulfonyl chloride, methanesulfonic anhydride. Ultimately, the aldehyde is obtained by addition of a suitable base to the reaction mixture, such as, for example, N,N-diethylethanamine, pyridine, sodium hydrogen carbonate.

The intermediates of formula (XXIV) in turn can be prepared by oxidizing an intermediate of formula (XXV).

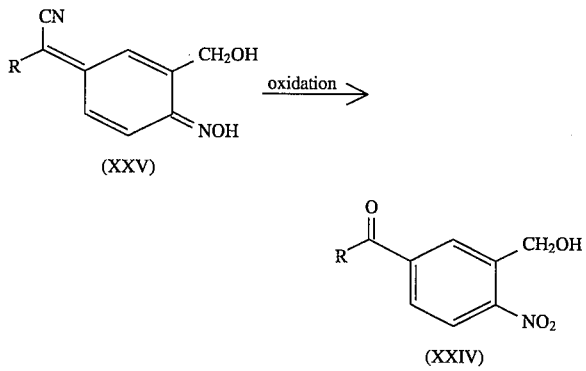

The intermediates of formula (XIV) wherein $>C=X$ is a radical of formula (b) or (c), said intermediate being represented by formulae (XIV-b) and (XIV-c), can be obtained by oxidizing the corresponding alcohol intermediate of formulae (XXVI-b) or (XXVI-c), following the procedures described hereinabove for the preparation of the intermediates of formula (XIV-a) from the corresponding alcohol of formula (XXIV).

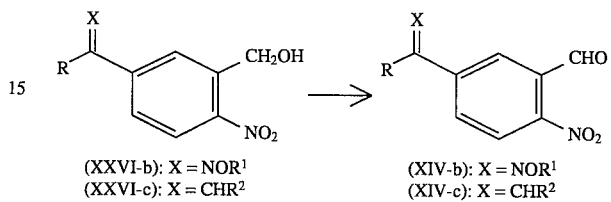

(XXVI-b): X = NOR$^1$
(XXVI-c): X = CHR$^2$ (XIV-b): X = NOR$^1$
(XIV-c): X = CHR$^2$

The preparation of the intermediates of formula (XXVI-b) wherein R is hydrogen, is described in EP-A-0,406,958, published Jan. 9, 1991.

The intermediate benzylalcohols of formula (XXVI-b) and (XXVI-c) can be derived from a protected alcohol (XXVII-b) or (XXVII-c) by art-known deprotection procedures.

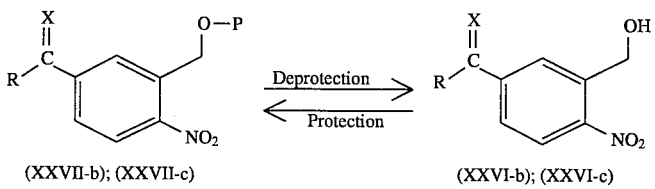

(XXVII-b); (XXVII-c)

(XXVI-b); (XXVI-c)

Said oxidation reaction can conveniently be conducted by stirring the reactants in water in the presence of an oxidizing agent such as, for example, hydrogen peroxide and the like, and a base such as, for example, potassium hydroxide and the like.

The intermediate of formula (XXV) in turn can be obtained by the addition of an intermediate of formula (XX) to 2-hydroxymethylnitrobenzene.

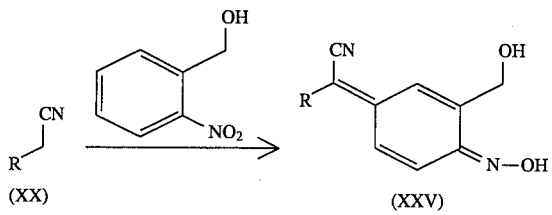

Said addition reaction can conveniently be conducted by stirring reactants in a reaction-inert solvent in the presence of an appropriate base. Suitable solvents are, for example, dipolar aprotic solvents, e.g. N,N-dimethylformamide, N,N-dimethylacetamide, dimethyl sulfoxide, pyridine and the like or alcohols, e.g. methanol and the like. Appropriate bases are sodium hydroxide, potassium hydroxide, sodium hydride, sodium amide, sulfinyl bis(methane) sodium salt and the like bases. Alternatively, said addition reaction may be carried out by applying art-known conditions of phase transfer catalysis reactions. Said conditions comprise stirring the reactants, with an appropriate base, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts.

In formula (XXVII-b) and (XXVII-c) P represents a suitable protective group such as, for example, tetrahydropyranyl, 2-methoxyethoxymethyl, 2-methoxypropyl, 2-acetoxypropyl, 1-ethoxyethyl and the like; a trialkylsily group, e.g. trimethylsily, tert. butyldimethylsilyl and the like groups. Said deprotection reaction can easily be conducted following art-known methods of hydrolyzing acetals and silyl ethers, e.g. by acid hydrolysis in aqueous media.

The intermediates of formula (XXVII-b) and (XXVII-c) wherein $>C=X$ is a radical of formula (b) or (c) can easily be prepared from an intermediate of formula (XXVII-a) wherein X or O, following the procedures described above for the conversion of the compounds of formula (I-a) into the compounds of formula (I-b) and (I-c).

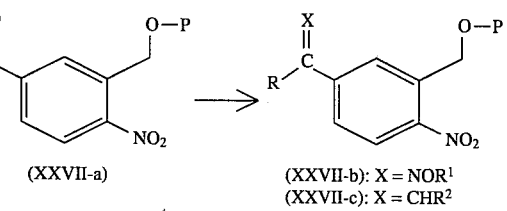

(XXVII-a)

(XXVII-b): X = NOR$^1$
(XXVII-c): X = CHR$^2$

The protected intermediates of formula (XXVII-a) may be obtained from the alkanols of formula (XXIV) following art-known procedures for protecting hydroxy groups. Typically such protection reactions may comprise treatment with a vinylether, e.g. dihydropyran, in an inert solvent and in the presence of an acid catalyst; or O-alkylation or O-silylation with a suitable alkylating reagent such as, for example, a trialkylsilyl halide, e.g. trimethylsilylchloride, tert. butyldimethylsilylchloride; and the like protection reactions.

The intermediate of formula (XXVI-b-1) wherein R is pyridinyl and X is $NOR^1$ wherein $R^1$ is other than hydrogen, said radical represented by formula $R^{1-a}$, can be obtained from the intermediates of formula (XXVI-b), wherein R is pyridinyl and X is NOH, said intermediates being represented by (XXVI-b-2) by O-alkylation or O-silylation following the procedures described hereinabove for the preparation of the compounds of formula (I-b-1).

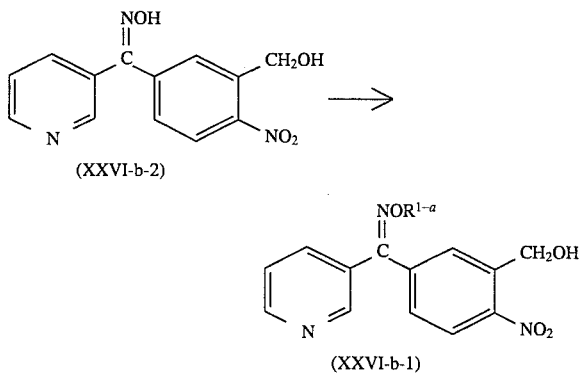

The intermediate of formula (XXVI-b-2) can be prepared by reducing the corresponding aldehyde of formula (XIV-b), wherein R is pyridinyl and X is NOH, said intermediate being represented by formula (XIV-b-2), following art-known reduction procedures

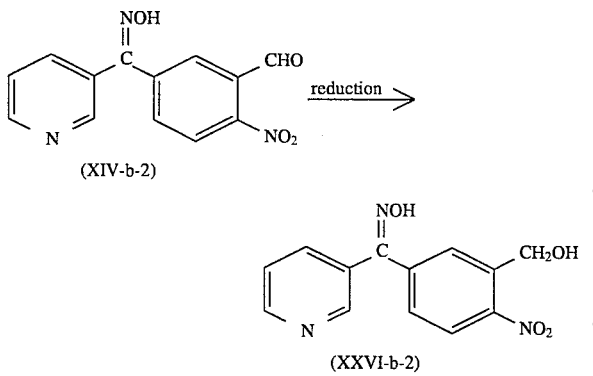

Said reduction reaction can conveniently be conducted by stirring the reactant or preferably a salt thereof, in an alkanol e.g. methanol and the like, in the presence of a reducing agent such as, for example, sodium borohydride and the like. A base, such as, for example, sodium hydroxide and the like is advantageously added to the reaction mixture in order to form a salt of the reactant.

The intermediates of formula (XIV-b-2) in turn can be obtained by hydrolyzing an intermediate of formula (XXVIII) in an acidic aqueous medium.

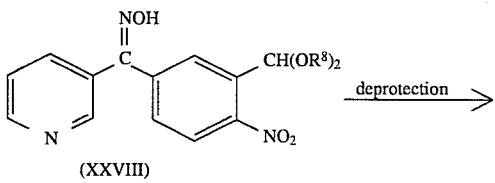

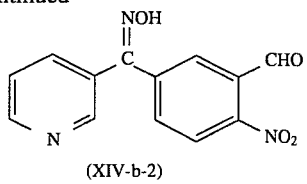

The intermediates of formula (XXVIII) can easily be prepared from an intermediate of formula (XXIX) wherein X is O and R is pyridinyl, following the procedures described hereinabove for the conversion of the compounds of formula (I-a) into the compounds of formula (I-b).

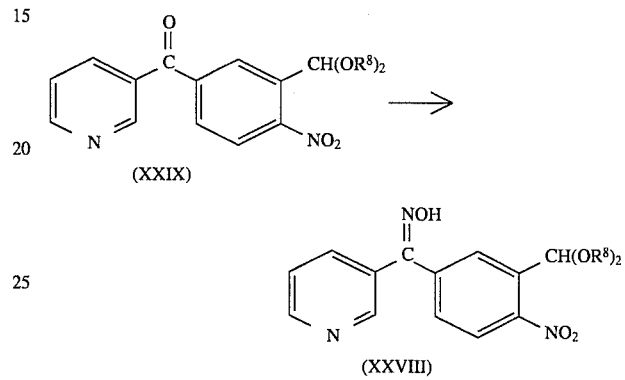

The protected intermediates of formula (XXIX) can be obtained selectively from the aldehydes of formula (XIV-a) wherein R is pyridinyl, said intermediates being represented by formula (XIV-a) following art-known procedures.

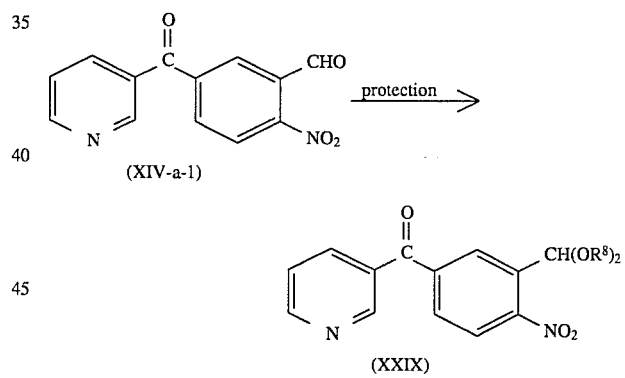

Typical such protection reactions comprise treatment with an alcohol, e.g. methanol, ethanol, 1,2-ethanediol and the like, in the presence of an acid catalyst, e.g. 4-methylbenzenesulfonic acid.

Alternatively, the intermediates of formula (XIV-b-1) can also be prepared by direct O-alkylation of the intermediates of formula (XXVIII), following the procedures described hereinabove for the preparation of the compounds of formula (I-b-1) and subsequently hydrolyzing the acetal group to an aldehyde in an aqueous acidic medium

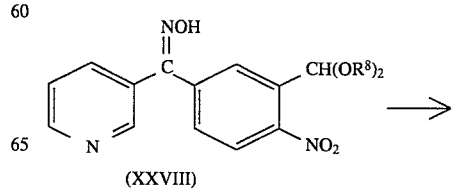

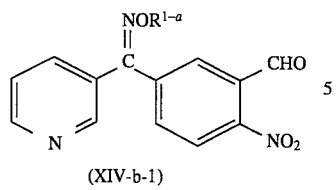

(XIV-b-1)

The intermediate of formula (XIV-c), wherein R is pyridinyl, said intermediates being presented by formula (XIV-c-1) can be obtained by hydrolyzing an intermediate of formula (XXX) in an acidic aqueous medium, following procedures described hereinabove for the preparation of the intermediates of formula (XIV-b-2).

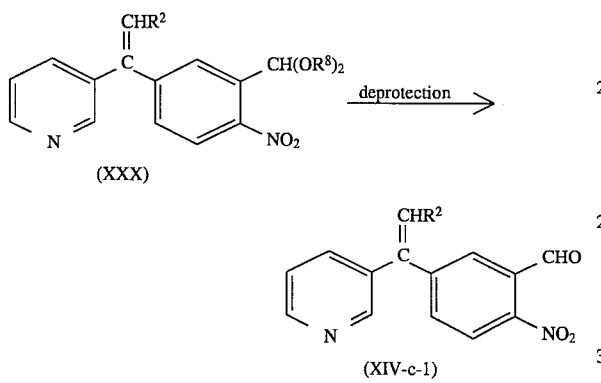

The intermediate of formula (XXX) in turn can easily be prepared from an intermediate of formula (XXIX) following the procedures described above for the conversion of the compounds of formula (I-a) into the compounds of formula (I-c).

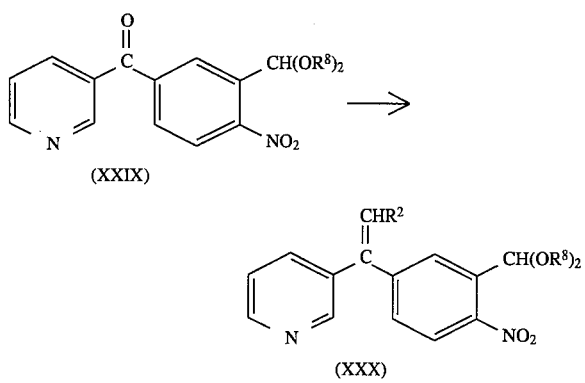

The intermediates of formula (IV) can be prepared by reducing an intermediate of formula (XXXI) following art-known procedures.

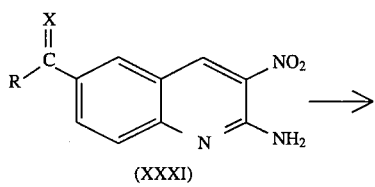

(XXXI)

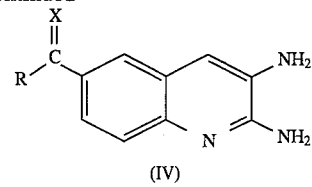

(IV)

A suitable reducing agent in the above reaction is, for example, tin(II)chloride in the presence of an acid, e.g. hydrochloric acid, or hydrogen in the presence of a hydrogenation catalyst.

The intermediates of formula (XXXI) can be prepared by reacting an intermediate of formula (XXXII) with nitroacetonitrile (XXXIII) in a reaction inert solvent, such as an alcohol, e.g. methanol, ethanol and the like.

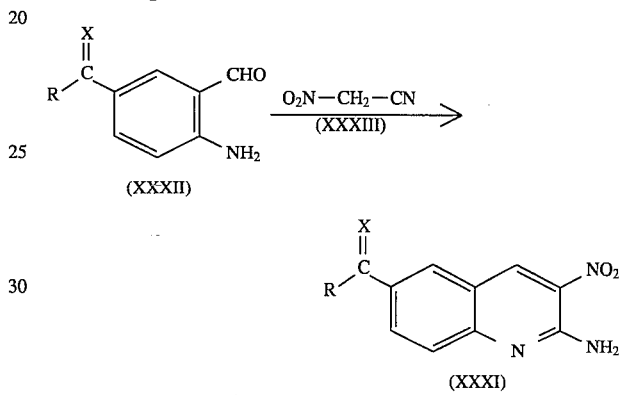

Alternatively, the intermediates of formula (XXXI) may be prepared by reacting the intermediates of formula (XXXIV) with $NH_3$ in a reaction-inert solvent, such as an alcohol, e.g. ethanol, 1-butanol and the like, preferably at an elevated temperature, e.g. the reflux temperature; or by reacting intermediates of formula (XXXIV) with ammonium acetate in acetic acid.

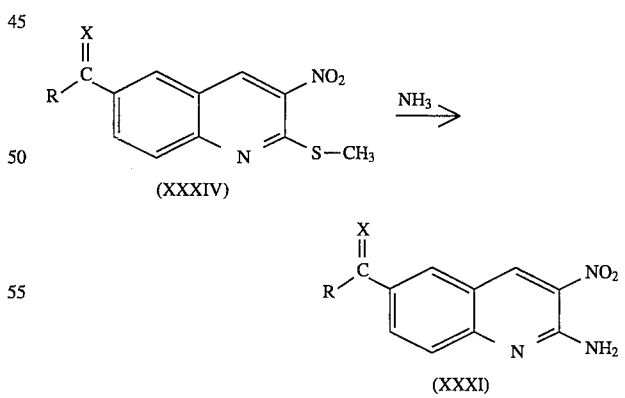

In a further alternative, the intermediates of formula (XXXI) can be prepared by the following reaction procedures:

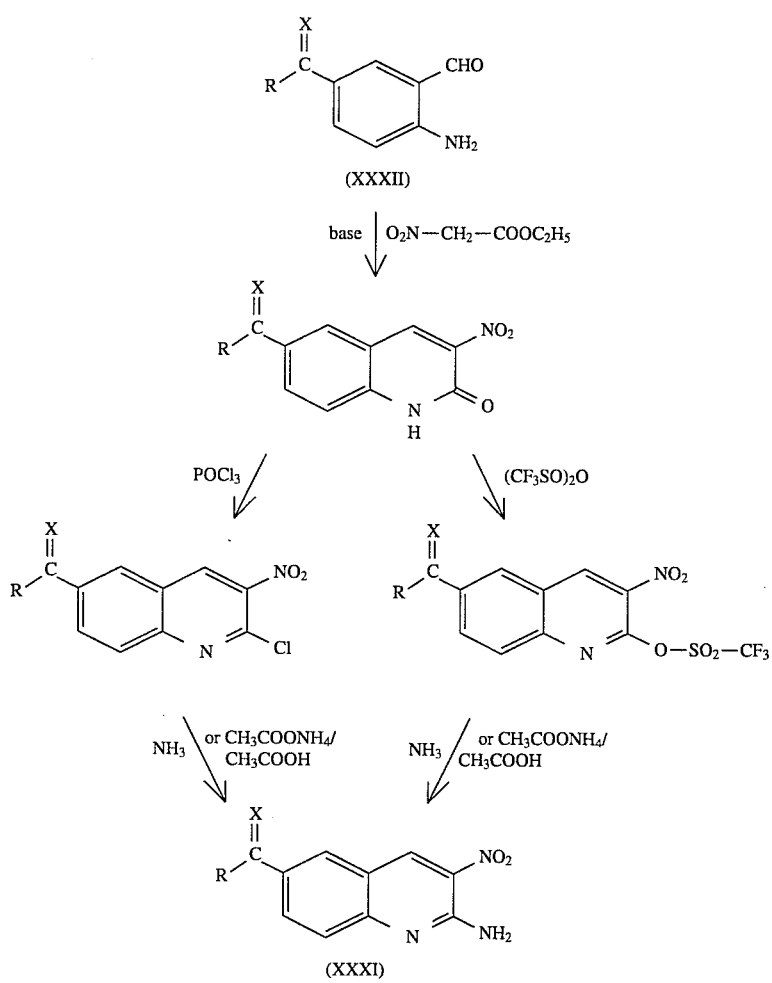

The intermediates of formula (XXXII) may be prepared by reducing the corresponding nitro-derivatives of formula (XIV) following art-known procedures.

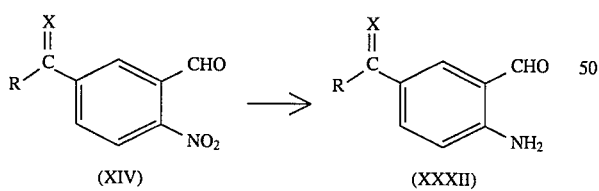

A suitable reducing agent in the above reaction is, for example, a metal, e.g. iron or zinc, in the presence of an acid, e.g. hydrochloric acid, or hydrogen in the presence of a hydrogenation catalyst.

The intermediate of formula (XXXIV) may be prepared by reacting the intermediates of formula (XXXII) with 1,1-bis(methylthio)-2-nitro-ethne (XXXV) in the presence of an acid, e.g. hydrochloric acid, methanesulphinic acid and the like.

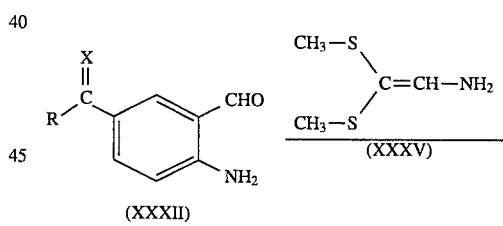

The compounds of formula (I) stereochemically isomeric forms thereof, are potent inhibitors of both the phosphodiesterase (PDE) family III (cGMP-inhibited family) and family IV (cAMP-specific family). The designation PDE III and PDE IV as used hereinafter refers to the classification by J. A. Beavo and D. H. Reifsnyder, TIPS Reviews, April 1990, pp 150–155.

Inhibition of phosphodiesterase isoenzymes of families III and IV leads to an elevation of cAMP levels in particular cells such as the cardiac muscle, certain lymphocyes, e.g. basophils and eosinophils, and mast-cells. cAMP is a key second messenger, the concentration of which affects particular cell activities through activation of enzymes such as kinases. A number of allergic and atopic disease are deemed to be caused by higher-than-normal PDE concentrations which result in low cAMP levels and hypersensitivity of the thus affected cells for excitatory stimuli. (Examples of said hypersensitivity are for example, excessive histamine release from basophils and mast cells or excessive superoxide anion radical formation by eosinophils). Hence, the present compounds having potent phosphodiesterase inhibitory properties are deemed useful agents in alleviating and/or curing allergic and atopic diseases. The functional effects of PDE III and IV inhibitors are e.g. airway smooth muscle relaxation, platelet aggregation inhibition and inhibition of white blood cell mediator release.

Particularly important in this context in the finding that the dual activity of the present compounds on both PDE family III and family IV results in an excellent down regulation of cells such as basophils and mast cells.

Consequently, the subject compounds are considered to be valuable therapeutic drugs for treating warm-blooded animals, particularly humans, suffering from allergic disorders, atopic diseases and related afflictions. Examples of allergic diseases are bronchial asthma, cheilitis, conjunctivitis, contact dermatitis and eczema, irritable bowel disease, dehydroform eczema, urticaria, vasculitis, vulvitis; examples of atopic diseases are dermatitis and eczema, winterfeet, asthma, allergic rhinitis; and related afflications are, for example, psoriasis and other hyperprofilerative diseases.

In view of their useful phosphodiesterase inhibiting properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspension, syrups, elixirs and the solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

In the preparation of aqueous compositions, addition salts of the subject compounds are obviously more suitable due to their increased water solubility.

Alternatively, the compounds of formula (I) may be formulated in a suitable carrier, e.g. a cyclodextrin (CD) or in particular a cyclodextrin derivative such as the cyclodextrin derivatives described in U.S. Pat. No. 3,459,731, EP-A-149,197 or EP-A-197,571. Typically such derivatives comprise $\alpha$-, $\beta$- or $\Gamma$-CD wherein one or more hydroxylgroups are substituted with $C_{1-6}$alkyl, particularly methyl, ethyl or isopropyl; hydroxy$C_{1-6}$alkyl, particularly hydroxyethyl, hydroxypropyl or hydroxy-butyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl; carboxy$C_{1-6}$alkyloxy$C_{1-6}$alkyl, particularly carboxymethoxypropyl, carboxyethoxypropyl or $C_{1-6}$alkylcarbonyloxy$C_{1-6}$alkyl, particularly 2-acetyloxypropyl. Especially noteworthy as complexants and/or solubilizers are $\beta$-CD, 2,6-dimethyl-$\beta$-CD, 2-hydroxyethyl-$\beta$-CD, 2-hydroxyethyl-$\gamma$-CD, 2-hydroxypropyl-$\gamma$-CD and (2-carboxymethoxy)propyl$\beta$-CD and in particular 2-hydroxypropyl-$\beta$-CD. In the aforementioned cyclodextrin derivatives, the DS (degree of substitution, e.g. the average number of substituted hydroxy functions per glucose unit) preferably is in the range of 0.125 to 3, in particular 0.2 to 2, or 0.2 to 1.5. More preferably the DS ranges from about 0.2 to about 0.7, in particular from about 0.35 to about 0.5 and most particularly is about 0.4. The MS (molar degree of substitution, i.e. the average number of moles of the substituting agent per glucose unit) is in the range of 0.125 to 10, in particular of 0.3 to 3, or 0.3 to 1.5. More preferably the MS ranges from about 0.3 to about 0.8, in particular from about 0.35 to about 0.5 and most particularly is about 0.4. The most preferred cyclodextrin derivative for use in the compositions of the present invention is hydroxypropyl-$\beta$-cyclodextrin having a MS in the range of from 0.35 to 0.50 and containing less than 1.5% unsubstituted $\beta$-cyclodextrin.

Said compositions may conveniently be prepared by dissolving the cyclodextrin or ether derivative thereof in water and adding thereto a subject compound as well as other adjuvants and components such as, for example, sodium chloride, potassium nitrate, glucose, mannitol, sorbitol, sylitol and buffers such as, for example, phosphate, acetate or citrate buffers; and optionally concentrating or drying the solution by evaporation under reduced pressure or by lyophilization. The amount of the cyclodextrin or ether derivative thereof in the final composition generally ranges from about 1% to about 40% by weight, particularly form 2.5% to 25% and more particularly from 5% to 20%.

Application of the subject compositions may be, for example, by aerosol, e.g. with a propellant such as nitrogen, carbon dioxide, a freon, or without a propellant such as a pump spray, drops, or a semisolid such as a thickened compositions which can be applied by a swab. In particular applications, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In view of the usefulness of the subject compounds in the treatment of allergic and atopic diseases it is evident that the present invention provides a method of treating warm-blooded animals suffering from allergic and atopic diseases, said method comprising the systemic administration of a pharmaceutically effective amount of a compound of formula (I) or a pharmaceutically acceptable addition salt thereof in admixture with a pharmaceutical carrier. Those of skill in the treatment of allergic and atopic diseases could easily determine the effective daily amount from the test results presented here. In general it is contemplated that an effective daily amount would be from 0.01 mg/kg to 4 mg/kg body weight, more preferably from 0.04 mg/kg to 2 mg/kg body weight.

It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention.

EXPERIMENTAL PART

A. Preparation of the Intermediates

Example 1 a) A mixture of 114.5 g of sodium hydrogen sulfite and 500 ml of water was stirred for 15 min at room temperature. After cooling to 5° C. on an ice-bath, there were added dropwise 100 g of 2-methoxybenzaldehyde and, after stirring for 15 min, 95.8 g of morpholine. Next there was added a solution of 39.2 g of sodium cyanide in 100 ml of water. The mixture was stirred for 24 hours at 50° C. The product was extracted with dichloromethane and the extract was dried, filtered and evaporated. The residue was co-evaporated with methylbenzene, yielding 168.2 g (99.2%) of α-(3-methoxyphenyl)-4-morpholineacetonitrile (interm. 1)

b) To a stirred mixture of 35 g of sodium hydride in 1000 ml of N,N-dimethylformamide under nitrogen, there was added dropwise a solution of 168.2 g of intermediate (1) in 250 ml of N,N-dimethylformamide. Stirring was continued for 3 hours. At 10° C., there was added dropwise a solution of 152.9 g of 3-chloro-2-(dimethoxymethyl)-1-nitrobenzene (prepared as described in J 655 and J 693) in 250 ml of N,N-dimethylformamide. The mixture was stirred for 1 hour at 10° C. and overnight at room temperature. The reaction mixture was poured into ice-water and the product was extracted with dichloromethane. The extract was dried, filtered and evaporated. The residue was stirred in water, filtered off and taken up in a mixture of water and dichloromethane. The organic layer was separated, dried, filtered and evaporated. The residue was washed with hexane (3x), yielding 294.6 g (100%) of α-[3-dimethoxymethyl)-4-nitrophenyl]-α-(3-methoxyphenyl)-4-morpholineacetonitrile (interm. 2).

In a similar manner there were also prepared:

α-[3-(dimethoxymethyl)-4-nitrophenyl]-α-(4-fluorophenyl)-4-morpholineacetonitrile (interm. 3);

α-[3-(dimethoxymethyl)-4-nitrophenyl]-α-(4-methylphenyl)-4-morpholineacetonitrile (interm. 4); and α-[3-(dimethoxymethyl)-4-nitrophenyl]-α-(4-methylphenyl)-4-morpholineacetonitrile (interm. 5).

c) To a stirred mixture of 1200 ml of 2-propanol saturated with HCl and 500 ml of water there was added dropwise a solution of 294.6 of intermediate (2) in 700 ml of 1,4-dioxane. Stirring was continued for 20 hours at reflux temperature. After cooling, the reaction mixture was evaporated and the residue was stirred in water. The whole was neutralized with NH$_4$OH and the product was extracted with dichloromethane. The extract was dried, filtered and evaporated. The residue was purified by column chromatography (silica gel; CH$_2$Cl$_2$). The eluent of the desired fraction was evaporated and the residue was successively stirred in diisopropylether and recrystallized from 2-propanol. The product was filtered off, washed with diisopropylether and dried, yielding 56.3 g (28.6%) of 5-(3-methoxy-benzoyl)-2-nitrobenzaldehyde; mp. 84.0° C. (interm. 6).

In a similar manner there were also prepared:

5-(4-fluorobenzoly)-2-nitrobenzaldehyde; mp. 105.2° C. (interm. 7);

5-(3,4-dimethoxybenzoyl)-2-nitrobenzaldehyde; mp. 169.4° C. (interm. 8); and 5-(4-methoxylbenzoyl)-2-nitrobenzaldehyde; mp. 131.7° C. (interm. 9).

Example 2 a) A solution of 91 g of intermediate (24), 41.6 ml of trimethoxymethane, 9.9 ml of sulfuric acid, 0.66 g of 4-methylbenzenesulfonic acid, 1000 ml of methanol and 50 ml of 2,2-dimethoxypropane was refluxed overnight. The cooled reaction mixture was poured into a mixture of 53 g of Na$_2$CO$_3$ in methanol, while stirring and cooling. The whole was filtered and the precipitate was rinsed with dichloromethane. The combined filtrates were evaporated and the residue was partitioned between water and dichloromethane. The organic layer was separated, dried, filtered and evaporated, yielding 106 g 98.8%) of [3-(dimethoxymethyl)-4-nitrophenyl](3-pyridinyl)methanone (interm. 10).

b) To a mixture of 106 g of intermediate (10), 700 ml of pyridine and 38.9 g of sodium hydrogen carbonate there were added 29.26 g of hydroxylamine monohydrochloride. The mixture was heated at 80°–90° C. overnight and was then evaporated. The residue was co-evaporated with ethanol (3x) and was then partitioned between water and dichloromethane. A precipitate was formed and filtered off in two fractions of resp. 32.1 g and 33.8 g of product. The organic layer of the filtrate was separated, dried, filtered and evaporated, yielding a third fraction of 27 g product. The second and third product fractions were combined and recrystallized from acetonitrile. The product was filtered off, washed with acetonitrile and dried in vacuo at 50°–60° C., yielding 44.7 g (40.1%) of (E/Z 85:15)-[3-(dimethoxymethyl)-4-nitrophenyl](3-pyridinyl)methanone, oxime (interm. 11). The first product fraction was taken up in a mixture of methanol and dichloromethane (90:10). This solution was washed with water, dried, filtered and evaporated. The residue was recrystallized from acetonitrile, yielding 10.6 g (9.5%) of (Z)-[3-(dimethoxymethyl)-4-nitrophenyl](3-pyridinyl)methanone, oxime; mp. 183.6° C. (interm. 12).

c) A mixture of 177 g of intermediate (11), 400 ml of hydrochloric acid 2N and 400 ml of 2-propanol was stirred overnight at 50° C. After cooling, the precipitate (=HCl salt of the Z-isomer) was filtered off and the filtrate was evaporated. The residue was stirred in water, filtered off and dried, yielding 18.1 g (10.5%) of (E)-5-[hydroxyimino)-(3-pyridinyl)methyl]-2-nitrobenzaldehyde monohydrochloride; mp. 230.6° C. (interm. 13).

In a similar manner there was also prepared:

ethyl (Z)-5-[[[(3-formyl-4-nitrophenyl)(3-pyridinyl)methylene]amino]oxy]pentanoate (interm. 14).

d) To a mixture of 13.5 g of intermediate (13) in 150 ml of water there were added dropwise 43.9 ml of sodium hydroxide 1N. After stirring for 5 min, the product was filtered off, washed with water and dried in vacuo at 60° C., yielding 11.15 g (93.6%) of (E)-5-[(hydroxyimino)(3-pyridinyl)methyl]-2-nitrobenzaldehyde (interm. 15).

e) To a stirred solution of 9.15 g of intermediate (15) in 100 ml of methanol and 35.3 ml of sodium hydroxide 1N there were added 0.45 g of sodium borohydride. Stirring at room temperature was continued until completion of the reaction and then there were added 2.67 g of ammonium chloride. After 15 min. the reaction mixture was evaporated and the residue was stirred in water. The product was filtered off, washed with water and dried in vacuo at 60° C., yielding 8.75 g (90.7%) of (E)-[3-(hydroxymethyl)-4-nitrophenyl](3-pyridinyl)methanone, oxime (interm. 16).

f) To a stirred solution of 8.75 g of intermediate (16) in 150 ml of N,N-dimethylformamide there were added portionwise 1.93 g of sodium hydride and, after 10 min. dropwise a solution of 5.4 ml of ethyl 5-bromopentanoate in 20 ml of N,N-dimethylformamide. The mixture was stirred overnight at room temperature and was then concentrated. The residue was taken up in a mixture of water (+NaCl) and dichloromethane. The product was extracted with dichloromethane and the extract was dried, filtered and evaporated. The residue was purified by column chromatography (silica gel; $CH_2Cl_2/C_2H_5OH$ 97:3). The eluent of the desired fraction was evaporated and the residue was co-evaporated with methylbenzene, yielding 13.0 g (100%) of ethyl (E)-5-[[[[3-(hydroxymethyl-4-nitrophenyl](3-pyridinyl)methylene]aminooxy]penanoate (interm. 17).

In a similar manner there were also prepared:

ethyl (E)-2-[[[[3-(hydroxymethyl)-4-nitrophenyl]methylene]amino]oxy]acetate; mp. 112.8° C. (interm. 18);

ethyl (Z)-5-[[[[3-(dimethoxymethyl)-4-nitrophenyl](3-pyridinyl)methylene]amino]oxy]pentanoate (interm. 19);

(E)-1-(cyclohexylmethyl)-4-[[[[[3-hydroxymethyl)-4-nitrophenyl]methylene]amino]oxy]acetyl]piperazine; 185.0° C. (interm. 54); and (E)-N-cyclohexyl-2-[[[[3-hydroxymethyl)-4-nitrophenyl]methylene]amino]oxy]-N-methylacetamide; mp. 169.5° C. (interm. 58).

Example 3

86.2 g of (E+Z)-N-cyclohexyl-2-[[[[3-(hydroxymethyl)-4-nitrophenyl]phenylmethylene]amino]oxy]-N-methylacetamide (prepared as described in U.S. Ser. No. 529,826) was separated into its E and Z isomers by column chromatography (Lichroprep Si60; $CH_2Cl_2/CH_3OH$ 98.5:1.5). The eluent of first fraction was evaporated and the residue was recrystallized from 2-propanol. The product was filtered off, washed with 2-propanol and hexane and dried, yielding 30.5 g (35.8%) of the (Z)-isomer, mp. 153.8° C. (interm. 20). Evaporation of the eluent of the second fraction yielded 25.9 g (30.4%) of the (E)-isomer (interm. 21).

Example 4 a) To a solution of 241.3 g of potassium hydroxide in 1400 ml of methanol there were added 130 g of 3-pyridineacetonitrile and a solution of 153 g of 2-nitrobenzenemethanol in 300 ml of methanol. After stirring for 1½ hour at room temperature, the reaction mixture was concentrated. To the residue there were added some ice-water and 300 g of acetic acid. The precipitate was filtered off, boiled in dichloromethane and further purified by column chromatography (silica gel; $CHCl_3/CH_3OH$ 90:10). The eluent of the desired fraction was evaporated and the residue was crystallized from a mixture of acetonitrile and methanol. After evaporation of the methanol, the product was filtered off, washed with diisopropylether and dried, yielding 67.9 g (25.9%) of (E+Z)-α-[4-(hydroxyimino)-3-(hydroxymethyl)-2,5-cyclohexadienylidene]-3-pyridineacetonitrile hemihydrate; mp. 199.7° C. (interm. 22).

b) To a solution of 982 g of potassium hydroxide in 5140 ml of water there were added 164.8 g of intermediate (22) and dropwise a solution of 988.8 ml of hydrogen peroxide in 2400 ml of water. After stirring for 3 hours, the precipitate was filtered off and washed successively with water, 2-propanol and diisopropylether. The product was purified by column chromatography (silica gel: $CHCl_3/CH_3OH$ 90:10). The eluent of the desired fraction was evaporated and the residue was crystallized from a mixture of acetonitrile and methanol. The product was filtered off and dried, yielding 53.4 g (31.8%) of [3-(hydroxymethyl)-4-nitrophenyl](3-pyridinyl)methanone; mp. 184.3°°C. (interm. 23).

c) To a solution of 18 g of intermediate (23) in 1000 ml of dichloromethane and 300 ml of dimethyl sulfoxide there were added 60 g of manganese(IV)oxide. After stirring overnight at room temperature, the mixture was filtered over diatomaceous earth. The filtrate was again stirred overnight with a new portion of 60 g of manganese(IV)oxide and then refluxed for 2 weeks. The reaction mixture was filtered over diatomaceous earth and the filtrate was concentrated. The residue was purified twice by column chromatography (silica gel; $CH_2Cl_2/CH_3OH$ 98:2). The eluent of the first and second fractions was evaporated, yielding 13.4 g (74.7%) of 2-nitro-5-(3-pyridinylcarbonyl)benzaldehyde (interm. 24)

In a similar manner there are also prepared:

(Z)-N-cyclohexyl-2-[[[(3-formyl-4-nitrophenyl)phenylmethylene]amino]oxy]-N-methylacetamide (interm. 25);

(E)-N-cyclohexyl-2-[[[(3-formyl-4-nitrophenyl)phenylmethylene]amino]oxy]-N-methylacetamide (interm. 26);

ethyl (E)-2-[[[(3-formyl-4-nitrophenyl)phenylmethylene]amino]oxy]acetate; mp. 105° C. (interm. 27); and ethyl (E)-5-[[[(3-formyl-4-nitrophenyl)(3-pyridinyl)methylene]amino]oxy]pentanoate (interm. 28).

d) A solution of ethanedioyl dichloride (0.042 mol) in dichloromethane (20 ml) was cooled to 31 70° C. (2-propanone/$CO_2$-bath), while stirring under $N_2$ flow. A solution of dimethyl sulfoxide (0.066 mol) in dichloromethane (7 ml) was added dropwise. The mixture was diluted with dichloromethane (80 ml). Intermediate (54) (0.0215 mol) was added portionwise, followed by tetrahydrofuran (25 ml). The reaction mixture was stirred for 15 min. N,N-diethylethanamine (0.128 mol) was added dropwise. The reaction temperature was allowed to rise to room temperature. The reaction mixture was washed once with water and twice with an aqueous NaOCl solution. The organic layer was separated, dried ($MgSO_4$), filtered and the solvent was evaporated. Toluene was added to the residue and the solvent was evaporated again, yielding 11.7 g (100%) of (E)-1-(cyclohexylmethyl)-4-[[[[(3-formyl-4-nitrophenyl)methylene]amino]oxy]acetyl]piperazine (interm. 55).

In a similar way was prepared:

(E)-N-cyclohexyl-2-[[[(3-formyl-4-nitrophenyl)methylene]amino]oxy]-N-methylacetamide (interm. 59).

e) To a stirred solution of 0.73 of sodium in 200 ml of ethanol there were added 7.49 g of diethyl 2,5-dioxoimidazolidine-4-phosphate and, after 5 min, a solution of 7.4 g of intermediate (24) in a mixture of 60 ml of ethanol and 90 ml of dichloromethane. Stirring at room temperature was continued for ½ hour. The reaction mixture was evaporated and the residue was stirred in water. The product was filtered off, washed with water and dried in vacuo at 60°–80° C., yielding 6.65 g (66.2%) of (E+Z)-5-[[2-nitro-5-(3-pyridinylcarbonyl)phenyl]methylene]-2,4-imidazolidinedione hemihydrate; mp. 199.4° C. (interm. 29).

The intermediates listed in Table 1 hereinbelow were prepared in the same manner.

[2[Z, 3 (E)]]-2-[[[[4-amino-3-[(2,5-dioxo-4-imidazolidinylidene)methyl]phenyl]phenylmethylene]amino]oxy]-N-cyclohexyl-N-methylacetamide (interm. 43);

ethyl [2[E, 3 (E+Z)]]-2-[[[[4-amino-3-[(2,5-dioxo-4-imidazolidinylidene) methyl]phenyl]methylenen]amino]oxy] acetate (interm. 44); and ethyl [5[E, 3 (E+Z)]]-5-[[[[4-amino-3-[2.5-dioxo-4-imidazolidinylidene) methyl]phenyl](3-pyridinyl)methylene] amino]oxy]pentanaoate (interm. 45).

TABLE 1

| Int. No. | X | R | Physical data |
|---|---|---|---|
| 30 | O | $C_6H_5-$ | mp. 214.5° C./E + Z |
| 31 | N—O—(CH$_2$)$_4$—COOC$_2$H$_5$ | 3-pyridinyl | [5[Z, 3 (E/Z)]] |
| 32 | N—O—CH$_2$—C(=O)—N(CH$_3$)(cyclohexyl) | $C_6H_5-$ | [2[Z, 3 (E)]] |
| 33 | N—O—(CH$_2$)$_4$—COOC$_2$H$_5$ | 3-pyridinyl | [5[E/Z, 3 (E/Z)]] |
| 34 | O | 3,4-(CH$_3$O)$_2$—C$_6$H$_3-$ | mp. 236.0° C./½H$_2$O/ E + Z |
| 35 | N—O—CH$_2$—C(=O)—N(CH$_3$)(cyclohexyl) | $C_6H_5-$ | [2[E, 3 (E + Z)]] |
| 36 | N—O—CH$_2$—COOC$_2$H$_5$ | H | [2[E, 3 (E + Z)]] |
| 37 | N—O—(CH$_2$)$_4$—COOC$_2$H$_5$ | 3-pyridinyl | [5[E, 3 (E + Z)]] |
| 38 | O | 4-F—C$_6$H$_4-$ | mp. 252.5° C./E + Z |
| 39 | O | 4-CH$_3$O—C$_6$H$_4-$ | mp. 215.7° C./E + Z |
| 40 | O | 4-CH$_3$—C$_6$H$_4-$ | mp. 220.4° C./E + Z |
| 56 | N—O—CH$_2$—C(=O)—N(piperazinyl)—CH$_2$—cyclohexyl | H | [2E, (E + Z)] |
| 60 | N—O—CH$_2$—C(=O)—N(CH$_3$)(cyclohexyl) | H | [2E, (E + Z)] | f) To a suspension of 5.85 g of a mixture of intermediate (29) and the free base thereof (42:58), 120 ml of tetrahydrofuran and 80 ml of water there were added 15 g of sodium dithionate. After completion of the reaction, the reaction mixture was evaporated. The residue was successively co-evaporated with a mixture of tetrahydrofuran/methylbenzene and methanol/methylbenzene, yielding 5.23 g (98.6%) of (E+Z)-5-[[2-amino-5-(3-pyridinylcarbonyl)phenyl]methylene]-2,4-imidazolidinedione (interm. 41).

In a similar manner there were also prepared:

ethyl [5[Z, 3 (E+Z)]]-5-[[[[4-amino-3-[(2,5-dioxo-4-imidazolidinylidene) methyl]phenyl](3-pyridinyl)methylene] amino]oxy]pentanoate (interm. 42);

Example 5

A mixture of 11.9 of intermediate (30), 2 ml of a solution of thiophene in methanol 4% and 250 ml of 2-methoxyethanol was hydrogenated overnight at normal pressure and room (temperature in the presence of 3 g of platinum-on-charcoal catalyst 5%. After the calculated amount of hydrogen was taken up, the catalyst was filtered off and the filtrate was evaporated. The residue was co-evaporated with methylbenzene and then stirred in diisopropylether. The product was filtered off, washed with diisopropylether and dried in vacuo at 80° C., yielding 10.8 g (99.6%) of (E+Z)-5-[(2-amino-5-benzoylphenyl)methylene]-2,4-imidazolidinedione (interm. 46).

In a similar manner there as also prepared:

(E+Z)-5-[[2-amino-5-(3-methoxybenzoyl)phenyl]methylene]-2,4-imidazolidinedione (interm. 47).

In a similar manner but using methanol as a solvent was prepared:

[2E,(E+Z)-1-[[[[[4-amino-3-[(2,5-dioxo-4-imidazolidinylidene)methyl]phenyl]methylene]amino]oxy]acetyl]-4-cyclohexylmethyl)piperazine (interm. 57);

In a similar manner but using tetrahydrofuran as a solvent was prepared:

[2E,(E+Z)-2-[[[[[4-amino-3-[(2,5-dioxo-4-imidazolidinylidene)methyl]phenyl]methylene]amino]oxy]-N-cyclohexyl-N-methylacetamide (interm. 61);

Example 6

A mixture of 9.8 g of intermediate (46) and 300 ml of 2-methoxyethanol was hydrogenated for 3 days at normal pressure and room temperature in the presence of 4 g of platinum-on-charcoal catalyst 5%. The catalyst was filtered off and the filtrate was evaporated. The residue was co-evaporated with methylbenzene, yielding 9.4 g (95.3%) of 5-[(2-amino-5-benzolylphenyl)methyl]-2,4-imidazolidinedione (interm. 48).

In a similar manner there was also prepared:

5-[[2-amino-5-(3,4-dimethoxybenzoyl)phenyl]methyl]-2,4-imidazolidinedione (interm. 49).

Example 7

A mixture of 8.5 g of intermediate (33), 4.94 g of iron powder, 4.73 g of ammonium chloride, 150 ml of ethanol, 75 ml of water and 100 ml of tetrahydrofuran was refluxed until no more intermediate was left. The reaction mixture was filtered while hot over diatomaceous earth. The filtrate was evaporated and the residue was taken up in 250 ml of a mixture of methanol and dichloromethane (10:90). The precipitate was filtered off and washed with a mixture of methanol and dichloromethane. The combined filtrates were filtered over diatomaceous earth and then washed with water (+NaCl), dried, filtered and evaporated, yielding 7.9 g (98.8%) of ethyl [5[(E+Z), 3(E+Z)]]-5-[[[[4-amino-3-[(2,5-dioxo-4-imidazolidinylidene)methyl]phenyl](3-pyridinyl)-methylene]amino]oxy]pentanoate (interm. 50).

In a similar manner there was also prepared:

[2[E, 3 (E+Z)]]-2-[[[[4-amino-3-[(2,5-dioxo-4-imidazolidinylidene)methyl]phenyl]phenylmethylene]amino]oxy]-N-cyclohexyl-N-methylacetamide (interm. 51).

Example 8

A mixture of 5.3 g of intermediate (38) and 250 ml of 2-methoxyethanol was hydrogenated at normal pressure and room temperature in the presence of 2 g of platinum-on-charcoal catalyst 5%. After a while, the catalyst was filtered off and replaced by a fresh amount of 2 g. After completion of the reaction, the catalyst was filtered off and the filtrate was evaporated. The residue was co-evaporated with methylbenzene, yielding 5 g (100%) of 5-[[2-amino-5-(4-fluorobenzoyl)phenyl]methyl]-2,4-imidazolidinedione (interm. 52).

In a similar manner there was also prepared:

5-[[2-amino-5-(4-methylbenzoyl)phenyl]methyl]-2,4-imidazolidinedione (interm. 53).

B. Preparation of the Final Compounds

Example 9

A solution of 9.4 g of intermediate (48), 7.6 g of 4-methylbenzenesulfonic acid and 90 ml of dimethyl sulfoxide was heated for ½ at 150°–160° C. The reaction mixture was poured into 600 ml of ice-water. The product was filtered off and stirred in an aqueous NaHCO₃ solution. The product was filtered off in two fractions of resp. 6.25 g and 0.28 g. The combined fractions were purified by column chromatography (HPLC; γ-amino propyl; CH$_2$Cl$_2$/CH$_3$OH 95:5). The eluent of the third and fourth fraction was evaporated and the residue was taken up in a mixture of methanol and water. There was added NaOH 1N while stirring and the whole was boiled for a few minutes with activated charcoal. The mixture was filtered while hot over diatonaceous earth. To the filtrate there was added HCl 1 N while stirring. The precipitate was filtered off, washed successively with a mixture of methanol and water (1:1), water, methanol and diisopropylether, and dried in vacuo at 70°–80° C., yielding 1.06 g (12.1%) of 7-benzoyl-1,3-dihydro-2h-imidazol[4,5-b]quinolin-2-one; mp. >300° C. (comp. 1)

In a similar manner there were also prepared:

7-(3,4-dimethoxybenzolyl)-1,3-dihydro-2H-imidazo[4,5-b]quinolin-2-one; mp. >300° C. (comp. 2);

7-(4-fluorobenzoyl)-1,3-dihydro-2H-imidazo[4,5-b]quinolin-2-one; mp. >300° C. (comp. 3); and 1,3-dihydro-7-(4-methylbenzoyl)-2H-imidazo[4,5-b]quinolin-2-one; mp. 22 300° C. (comp. 4).

Example 10

A mixture of 5.23 g of intermediate (41), 6.4 g of 4-methylbenzenesulfonic acid and 100 ml of dimethyl sulfoxide was heated at 150° C. for 40 min. The reaction mixture was poured into ice-water and NaHCO₃ 10% was added dropwise while stirring to a pH of 5. The precipitate was filtered off, washed with water and boiled three times in a mixture of ethyl acetate and methanol (1:1) (resp. 100 ml; 75 ml and 50 ml). Each time the product was filtered off while hot and washed with a mixture of ethyl acetate and methanol and with diisopropylether. Next the product was taken up in a mixture of 50 ml of methanol and 20 ml of water. The whole was boiled with 300 mg of activated charcoal. The mixture was filtered while hot over diatomaceous earth and to the cooled filtrate there were added 10 ml of HCl 1N while stirring. The precipitate was filtered off, washed successively with a mixture of water and methanol (1:1), water, methanol, and diisopropylether, and dried in vacuo at 70°–80° C., yielding 0.63 g (12.0%) of 1,3-dihydro-7-(3-pyridinylcarbonyl-2H-imidazo[4,5-b]quinolin-2-one monohydrate; mp. >300° C. (comp. 5).

The compounds listed in Table 2 hereinbelow were prepared in the same manner.

TABLE 2

(structure shown: quinoline-imidazolone with X=C substituent at position 7 bearing R group)

| Co. No. | X | R | Physical data |
|---|---|---|---|
| 6 | N—O—(CH$_2$)$_4$—COOC$_2$H$_5$ | 3-pyridinyl | mp. 232.4° C./½H$_2$O/Z |
| 7 | N—O—CH$_2$—C(=O)—N(CH$_3$)—cyclohexyl | C$_6$H$_5$— | mp. 241.6° C./Z |
| 8 | N—O—(CH$_2$)$_4$—COOC$_2$H$_5$ | 3-pyridinyl | E + Z |
| 9 | O | 3-CH$_3$O—C$_6$H$_4$— | mp. >300° C. |
| 10 | N—O—CH$_2$—C(=O)—N(CH$_3$)—cyclohexyl | C$_6$H$_5$— | mp. 234.3° C./½H$_2$O/E |
| 11 | N—O—CH$_2$—COOC$_2$H$_5$ | H | mp. >270° C. (decomp.)/E |
| 12 | N—O—(CH$_2$)$_4$COOC$_2$H$_5$ | 3-pyridinyl | mp. 288.2° C./E |

In a similar manner but using 1-[(4-methylphenyl)sulfonyl]pyridinium are prepared:

(E)-1-(cyclohexylmethyl)-4-[[[[(2,3-dihydro-2-oxo-1H-imidazo[4,5-b]quinolin-7-yl) methylene]amino]oxy]acetyl] piperazine monohydrate; mp. 22 260.0° C. (comp. 15); and (E)-N-(cyclohexyl-2-[[[(2,3-dihydro-2-oxo-1H-imidazo [4,5-b]quinolin-7-yl) methylene]amino]oxy]-N-methylacetamide hemihydrate; mp. 263.4° C. (comp. 16).

Example 11

A mixture of 0.99 g of compound (6) and 10 ml of sodium hydroxide 1N was stirred for 2½ hours at room temperature. To the reaction mixture there were added 10 ml of HCl 1N. The precipitate was filtered off, washed with water and boiled in methanol. The product, was filtered off, washed with methanol and diisopropylether and dried in vacuo at 80° C., yielding 0.7 g (75.1%) of (Z)-5-[[[(2,3-dihydro-2-oxo-1H-imidazo[4,5-b]-quinolin-7-yl) (3-pyridinyl)methylene]amino]oxy]pentanoic acid; mp. >300° C. (decomp.) (comp. 13).

In a similar manner there was also prepared:

(E+Z)-5-[[[(2,3-dihydro-2-oxo-1H-imidazo[4,5-b]quinolin-7-yl) (3-pyridinyl)-methylene]amino]oxo]pentanoic acid monohydrate; mp. 233.5° C. (comp. 14).

C) Pharmacological Examples

The alleviating and/or curing effect of the instant compounds on allergic and atopic diseases was assessed by an in vitro assay system to detect an inhibiting effect on the phosphodiesterase type III in human and canine muscle cells and a similar inhibiting effect on the phosphodiesterase type IV in human mononuclear lymphocytes.

Example 12: Inhibition of phosphodiesterase type III (PDE III)

The incubation mixture (pH 7.1) (200 μl) contained 40 mM Tris, 3.75 mM 2-mercaptoethanol, 6 mM magnesium chloride, 1.2 μM $^3$H-cAMP (310 mci/mmole) and the phosphodiesterase type III, the amount depending on the enzymatic activity. A protein concentration was chosen that showed a linear increase of phosphodiesterase activity during an incubation period of 10 minutes at 37° C.

When the effect of different compounds on phosphodiesterase activity was tested, the medium without cAMP was incubated with the compound(s) or its carrier (DMSO-1% final concentration) for 5 min. The enzymatic reaction was started by addition of $^3$H-cAMP and stopped 10 min later after transferring the tubes in a waterbath at 100° C. for 40 sec. After cooling to room temperature alkaline phosphatase (0.25 μg/ml) was added and the mixture was left at room temperature for 20 min. The mixture was subsequently applied to a 1 ml DEAE-Sephadex A-25 column (pasteur pipet) and washed twice with 3 ml 20 mM Tris-HCl at pH 7.4. The $^3$H-labelled reaction products in the eluate were quantified by liquid scintillation counting.

The inhibiting effect of the present compounds on canine and human heart phosphodiesterase PDE III was measured at different concentrations of the instant compounds. The IC$_{50}$ values were calculated graphically from the thus obtained inhibition values. Table 3 shows available IC$_{50}$ values of the present compounds on canine and human heart PDE III.

TABLE 3

| Comp. No. | Canine heart PDE III IC$_{50}$ (10$^{-6}$ M) | Human heart PDE III IC$_{50}$ (10$^{-6}$ M) |
|---|---|---|
| 1 | 0.01 | 0.042 |
| 2 | 0.033 | 0.086 |
| 3 | 0.037 | 0.036 |
| 4 | 0.026 | 0.018 |
| 5 | 0.042 | 0.12 |
| 6 | 0.03 | 0.044 |
| 7 | 0.032 | 0.027 |
| 9 | 0.021 | 0.018 |
| 10 | 0.014 | 0.017 |
| 11 | 0.026 | 0.039 |
| 12 | 0.029 | 0.033 |
| 13 | 0.084 | 0.049 |
| 14 | 0.1 | 0.1 |

Example 13: Inhibition of Phosphodiesteraes type IV from Human Mononuclear Lymphocytes (MNL)

Human blood was obtained from donor that were documented before to suffer from allergic or atopic disease, 35 ml of blood was obtained from the umbilical veins by venipuncture and collected in 5 ml 100 mM $K_2EDTA$ pH 7.1. 4 ml of 0.6% dextran in saline was added and the mixture was left at room temperature for 30 min. The red blood cell free supernatant was collected, layered gently on a Lymphoprep solution and centrifuged at 750 g for 15 min at 18° C. The interfase was collected, diluted with a buffer containing 137M NaCl, 50 mM KCl and 100 mM HEPES at pH 7.4, and centrifuged at 900 g for 10 min at 10° C. The resulting pellet was resuspended in the same buffer.

The suspension of MNLs was adjusted to 1T Triton X100 and 0.3% Brij35 and frozen in liquid $N_2$. After 3 freeze-thaw cycles, the suspension was homogenized at 4° C. in a Polytron PT3000 (Kinematica AG) homogenizer (PT-DA 3020/2 TX) at 8000 rpm for 5×10 sec, followed by sonication at 4° C. in a Branson sonifier 250 at a frequency output of 20000 Hz, working output 40 W for 10×30 sec. The homogenate was centrifuged at 10000 g for 10 min. The resulting supernatant was used as source for PDE IV activity. The incubation mixture (pH 7.1) (200 µl) contained 40 mM Tris, 3.75 mM 2-mercaptoethanol, 6 mM magnesium chloride, 1.2 µM $^3$H-cAMP (310 mCi/mmole) and the phosphodiesterase type IV, the amount depending on the enzymatic activity. A protein concentration was chosen and showed a linear increase increase of phosphodiesterase activity during an incubation period of 10 minutes at 37° C. and where less than 10% of the initial substrate was hydrolyzed. To block contaminating PDE III activity, PDE IV activity was measured in the presence of $10^{-4}$ M cGMP.

When the effect of different compounds on phosphodiesterase activity was tested, the medium without cAMP was incubated with the compound(s) or its carrier (DMSO-1% final concentration) for 5 min. The enzymatic reaction was started by addition of $^3$H-cAMP and stopped 10 min later after transferring the tubes in a waterbath at 100° C. for 40 sec. After cooling to room temperature, alkaline phosphatase (0.25 µg/ml) was added and the mixture was left at room temperature for 20 min. The mixture was subsequently applied to a 1 ml DEASE-Sephadex A-25 column (pasteur pipet) and washed twice with 3 ml 20 mM Tris-HCl at pH 7.4. The $^3$H-labelled reaction products in the eluate were quantified by liquid scintillation counting.

The inhibiting effect of the present compounds of human mononuclear lymphocyte phosphodiesterase PDE IV was measured at different concentrations of the instant compounds. The $IC_{50}$ values were calculated graphically from the thus obtained inhibition values. Table 4 shows available $IC_{50}$ values of the present compounds on human mononuclear lymphocyte PDE IV.

TABLE 4

| Comp. No. | Human MNL PDE IV $IC_{50}$ ($10^{-6}$ M) |
|---|---|
| 1 | 5.8 |
| 2 | 4.5 |
| 6 | 1.7 |
| 7 | 2.6 |
| 10 | 0.49 |
| 12 | 3.6 |

D) Composition Examples

The following formulation exemplify typical pharmaceutical compositions in dosage unit form suitable for systemic administration to animal and human subjects in accordance with the present invention.

"Active ingredient" (A.I.) as used throughout these examples relates to a compound of formula (I), a pharmaceutically acceptable acid addition salt or a stereochemically isomeric form thereof.

Example 14: Oral Drops 500 g of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example 15: Oral Solution 9 g of methyl 4-hydroxybenzoate and 1 g of propyl 4-hydroxybenzoate were dissolved in 4 l of boiling purified water. In 3 l of this solution were dissolved first 10 g of 2,3-dihydroxybutanedioic acid and thereafter 20 of the A.I. The latter solution was combined with the remaining part of the former solution and 12 l 1,2,3-propanetriol and 3 l of sorbitol 70% solution were added thereto, 40 g of sodium saccharin were dissolved in 0.5 l of water and 2 ml of raspberry and 2 ml of gooseberry essence were added. The later solution was combined with the former, water was added q.s. to a volume of 20 l providing an oral solution comprising 5 mg of the A.I. per teaspoonful (5 ml). The resulting solution was filled in suitable containers.

Example 16: Capsules 20 g of the A.I., 6 g sodium lauryl sulfate, 56 g starch, 56 g lactose, 0.8 colloidal silicon dioxide, and 1.2 g magnesium stearate were vigorously stirred together. The resulting mixture was subsequently filled into 1000 suitable hardened gelatin capsules, each comprising 20 mg of the A.I.

Example 17: Film-coated Tablets

Preparation of Tablet Core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel®) and 15 g hydrogenated vegetable oil (Sterotex®). The whole was mixed well and compressed into tablets, giving 10.000 tablets, each comprising 10 mg of the active ingredient.

Coating

To a solution of 10 g methyl cellulose (Methocel 60 HG®) in 75 ml of denaturated ethanol there was added a solution of 5 g of ethyl cellulose (Ethocel 22 cps®) in 50 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension (Opaspray K-1-2109®) and the whole was homogenated. The tablet cores were coated with the thus obtained mixture in a coating apparatus.

Example 18: Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration (U.S.P. XVII p. 811) and filled in sterile containers.

Example 19: Suppositories 3 g A.I. was dissolved in a solution of 3 g 2,3-dihydroxybutanedioic acid in 25 ml polyethylene glycol 400. 12 G surfactant (SPAN®) and triglycerides (Witepsol 555®) q.s. ad 300 g were molten together. The latter mixture was mixed well with the former solution. The thus obtained mixture was poured into moulds at a temperature of 37°–38° C. to form 100 suppositories each containing 30 mg of the active ingredient.

Example 20: 2% Cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70° to 75° C. while using a homogenizer for liquids. The resulting emulsion is allowed to cool to below 25° C. while continuously mixing. A solution of 20 mg A.I., 1 mg polysorbate 80 and purified water and a solution of 2 mg sodium sulfite anhydrous in purified water are next added to the emulsion while continuously mixing. The cream, 1 g of the A.I. is homogenized and filled into suitable tubes.

Example 21: 2% Topical Gel

To a solution of 200 mg hydroxypropyl β-cyclodextrine in purified water is added 20 mg of A.I. while stirring. Hydrochloric acid is added until complete dissolution and then sodium hydroxide is added until pH 6.0. This solution is added to a dispersion of 10 mg carrageenan PJ in 50 mg propylene glycol while mixing. While mixing slowly, the mixture is heated to 50° C. and allowed to cool to about 35° C. whereupon 50 mg ethyl alcohol 95% (v/v) is added. The rest of the purified water q.s and 1 g is added and the mixture is mixed to homogenous.

Example 22; 2% Topical Cream

To a solution of 200 mg hydroxypropyl β-cyclodextrime is purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alchol, 20 mg cetyl alcohol, 20 mg glycerol monostearate and 15 mg sorbate 60 having a temperature of 70° C. while mixing slowly. After cooling down to below 25° C., the rest of the purified water q.s. ad 1 g is added and the mixture is mixed to homogenous.

Example 23: 2% Liposome Formulation

A mixture of 2 g A.I. microfine, 20 g phosphatidyl choline, 5 g cholesterol and 10 g ethyl alcohol is stirred and heated at 55°–60° C. until complete dissolution and is added to a solution of 0.2 g methyl paraben, 0.02 g propyl paraben, 0.15 g disodium edetate and 0.3 g sodium chloride in purified water while homogenizing. 0.15 g Hydroxypropylmethylcellulose in purified water ad 100 g is added and the mixing is continued until swelling is complete.

Example 24: 2% Liposome Formulation

A mixture of 10 g phosphatidyl choline and 1 g cholesterol in 7.5 g ethyl alcohol is stirred and heated at 40° C. until complete dissolution. 2 g A.I. microfine is dissolved in purified water by mixing while heating at 40° C. the alcoholic solution is added slowly to the aqueous solution while homogenizing during 10 minutes. 1.5 g Hydroxypropylmethylcellulose is purified water is added while mixing until swelling is complete. The resulting solution is adjusted to pH 5.0 with sodium hydroxide 1N and diluted with the rest of the purified water ad 100 g.

Example 25: Aerosols a) To a solution of 0.1 g of hydroxypropyl β-cyclodextrin (MS=0.43) in 0.7 ml of distilled water were added 730 μg of a 0.1 N hydrochloric acid solution and 2.5 mg A.I.. After stirring for 10 minutes at room temperature, the pH of the thus obtained solution was adjusted to pH 5.5 by adding a 0.1 N sodium hydroxide solution. Then there were added successively 4 mg of sodium chloride and 0.15 mg of phenyl mercury acetate and the whole was stirred to produce complete dissolution. Distilled water was then added to a volume of 1.0 ml. The whole was filled in a glass bottle closed with a mechanical pump deliverying 0.1 ml per puff upon administration.

b) To a solution of 0.1 g of dimethyl β-cyclodextrin in 0.7 ml of distilled water were added 600 μg of a 0.1 N hydrochloric acid solution and 2 mg A.I.. After stirring for 10 minutes at room temperature, 10 mg of polyvinylalcohol was dissolved in the mixture and the pH of the thus obtained solution was adjusted to pH 5.5 by adding a 0.1 N sodium hydroxide solution. Then there were added successively 4 mg of sodium chloride and 2 mg of phenylethyl alcohol and the whole was stirred to produce complete dissolution. Distilled water was added to produce a volume of 1.0 ml which was filled in a glass bottle with a mechanical pump deliverying 0.1 ml per puff upon adminstration.

We claim:

1. A compound of the formula:

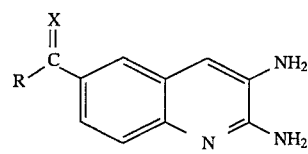

(IV)

an addition salt thereof or a stereochemically isomeric form thereof, wherein:

R represents hydrogen; $C_{1-6}$alkyl; $C_{3-6}$cycloalky; phenyl optionally substituted with from 1 to 3 substituents each independently selected from halo, hydroxy, $C_{1-6}$alkyloxy, $C_{5-6}$cycloalkyloxy, $C_{1-6}$alkyl or trifluoromethyl; pyridinyl; or thienyl optionally substituted with halo or $C_{1-6}$alkyl; and =C=X is a radical of the formula:

=C=O   (a),

=C=N—O—$R^1$   (b), or

=C=CH—$R^2$   (c);

$R^1$ represents hydrogen, tri($C_{1-6}$alkylsilyl or $C_{1-6}$alkyl optionally substituted with COOH, COO$C_{1-4}$alkyl, CONR$^3$R$^4$ or COOCH$_2$CONR$^5$R$^6$; and $R^2$ represents COOH, COO$C_{1-4}$alkyl, CONR$^3$R$^4$, COOCH$_2$CONR$^5$R$^6$ or $C_{1-6}$alkyl optionally substituted with COOH, COO$C_{1-4}$alkyl, CONR$^3$R$^4$ or COOCH$_2$CONR$^5$R$^6$, wherein in the foregoing:

$R^3$ represents hydrogen, $C_{1-4}$alkyl, hydroxy$C_{1-4}$alkyl, $C_{1-4}$alkyloxy$C_{1-4}$alkyl, hydroxy-carbonyl$C_{1-4}$alkyl, $C_{1-4}$alkyloxycarbonyl$C_{1-4}$alkyl;

$R^4$ represents hydrogen, $C_{1-4}$alkyl, hydroxy$C_{1-4}C_{1-4}$alkyl, $C_{3-7}$cycloalkyl, phenyl, thienyl or pyridinyl; or or $R^3$ or $R^4$ taken together with the nitrogen atom to which they are attached may form a pyrrolidinyl, morpholinyl or piperazinyl ring, said piperazinyl ring, said piperazinyl ring being optionally substituted on the nitrogen atom with $C_{1-4}$alkyl, $(C_{3-7}$cycloalkyl$)C_{1-4}$alkyl, phenyl$C_{1-4}$alkyl or $C_{1-6}$alkyl substituted with from one to five hydroxy groups;

$R^5$ is hydrogen, $C_{1-4}$alkyl, hydroxy$C_{1-4}$alkyl, $C_{1-4}$alkyloxy$C_{1-4}$alkyl, hydroxycarbonyl$C_{1-4}$alkyl, $C_{1-4}$alkyloxycarbonyl$C_{1-4}$alkyl;

$R^6$ is hydrogen, $C_{1-4}$alkyl, hydroxy$C_{1-4}$alkyl, $C_{3-7}$cycloalkyl, phenyl, thienyl or pyridinyl; or $R^5$ and $R^6$ taken together with the nitrogen atom to which they are attached may form a pyrrolidinyl, morpholinyl or piperazinyl ring, said piperazinyl ring said piperazinyl ring being optionally substituted on the nitrogen atom with $C_{1-4}$alkyl, $(C_{3-7}$cycloalkyl$)C_{1-4}$alkyl, phenyl$C_{1-4}$alkyl or $C_{1-6}$alkyl substituted with from one to five hydroxy groups.

2. A compound according to claim 1, wherein R is hydrogen; phenyl optionally substituted with 1 to 2 substituents each independently selected from halo, $C_{1-6}$alkyloxy, $C_{5-6}$cycloalkyloxy or $C_{1-6}$alkyl; or pyridinyl; and =C=X is a radical of formula (a) or (b).

3. A compound according to claim 2, wherein R is hydrogen; phenyl optionally substituted with 1 to 2 substituents each independently selected from fluoro, chloro, bromo, methoxy, cyclopentyloxy or methyl; or pyridinyl; and =C=X is a radical of formula (a) or (b), wherein $R^1$ is $C_{1-4}$alkyl optionally substituted with COOH, COOC$_{1-4}$alkyl or CONR$^3$R$^4$.

4. A compound according to claim 1, wherein R is hydrogen; phenyl optionally substituted with 1 to 2 substituents each independently selected from fluoro, methoxy or methyl; and =C=X is a radical of formula (a) or (b) wherein $R^1$ is $C_{1-4}$alkyl optionally substituted with COOH, COOC$_2$H$_5$, CON(CH$_3$)) (c.c$_6$H$_{11}$) or

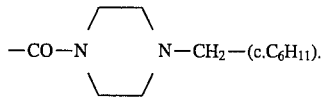

* * * * *